(12) United States Patent
Chenal

(10) Patent No.: US 11,826,231 B2
(45) Date of Patent: Nov. 28, 2023

(54) EARPIECE-FOAM SIZING APPARATUS AND METHOD

(71) Applicant: JMJ Holdings, LLC, Frederic, WI (US)

(72) Inventor: David M. Chenal, Frederic, WI (US)

(73) Assignee: JMJ Holdings, LLC, Frederic, WI (US)

( * ) Notice: Subject to any disclaimer, the term of this patent is extended or adjusted under 35 U.S.C. 154(b) by 0 days.

(21) Appl. No.: 17/785,799

(22) PCT Filed: Dec. 21, 2020

(86) PCT No.: PCT/US2020/066494
§ 371 (c)(1),
(2) Date: Jun. 15, 2022

(87) PCT Pub. No.: WO2021/133747
PCT Pub. Date: Jul. 1, 2021

(65) Prior Publication Data
US 2023/0058747 A1    Feb. 23, 2023

Related U.S. Application Data

(60) Provisional application No. 62/953,181, filed on Dec. 23, 2019.

(51) Int. Cl.
*A61F 11/08* (2006.01)
*A61F 2/00* (2006.01)

(52) U.S. Cl.
CPC .......... *A61F 11/085* (2022.01); *A61F 2/0095* (2013.01); *A61F 2240/002* (2013.01); *A61F 2240/005* (2013.01)

(58) Field of Classification Search
CPC ........ A42B 3/16; A61F 13/2017; A61F 11/30; A61F 11/10; A61F 11/085; A61F 2/0095; A61F 2240/002; A61F 2240/005
See application file for complete search history.

(56) References Cited

U.S. PATENT DOCUMENTS

| | | | |
|---|---|---|---|
| 4,498,469 A | 2/1985 | Csiki | |
| 5,044,463 A * | 9/1991 | Carr | A61F 11/08 181/135 |
| 5,609,164 A | 3/1997 | Dyrud et al. | |

(Continued)

OTHER PUBLICATIONS

"PCT international Preliminary Report on Patentability for parent PCT/US2020/066494 application, dated Feb. 2, 2022, 31 pages."

*Primary Examiner* — Joseph S Del Sole
*Assistant Examiner* — Margaret B Hayes
(74) *Attorney, Agent, or Firm* — Charles A. Lemaire; Jonathan M. Rixen; Lemaire Patent Law Firm, P.L.L.C.

(57) ABSTRACT

The present invention provides system for shaping at least a foam portion of an earpiece, the system including a sizer configured to receive at least the foam portion of the earpiece such that at least the foam portion of the earpiece is reduced in size before being placed into an ear of a user, wherein the sizer includes a hollow structure having an open first end and a second end, wherein the first end has a first cross-sectional area, wherein the second end has a second cross-sectional area, and wherein the first cross-sectional area is larger than the second cross-sectional area.

20 Claims, 20 Drawing Sheets

(56) References Cited

U.S. PATENT DOCUMENTS

| | | | |
|---|---|---|---|
| 7,236,605 B2 | 6/2007 | Oliviera et al. | |
| 7,967,015 B2 | 6/2011 | Jenkins | |
| 8,327,973 B2 | 12/2012 | Parish et al. | |
| 8,960,366 B2 | 2/2015 | Peskar et al. | |
| 9,092,965 B2 | 7/2015 | Lyons et al. | |
| 9,603,746 B2 | 3/2017 | Chenal | |
| 11,413,631 B2 * | 8/2022 | Meirav | B04C 5/185 |
| 2005/0087195 A1 * | 4/2005 | Huang | A61F 11/12 |
| | | | 128/864 |
| 2011/0146420 A1 * | 6/2011 | Okada | A61B 10/0038 |
| | | | 73/864.51 |
| 2015/0335489 A1 | 11/2015 | Hamer et al. | |

\* cited by examiner

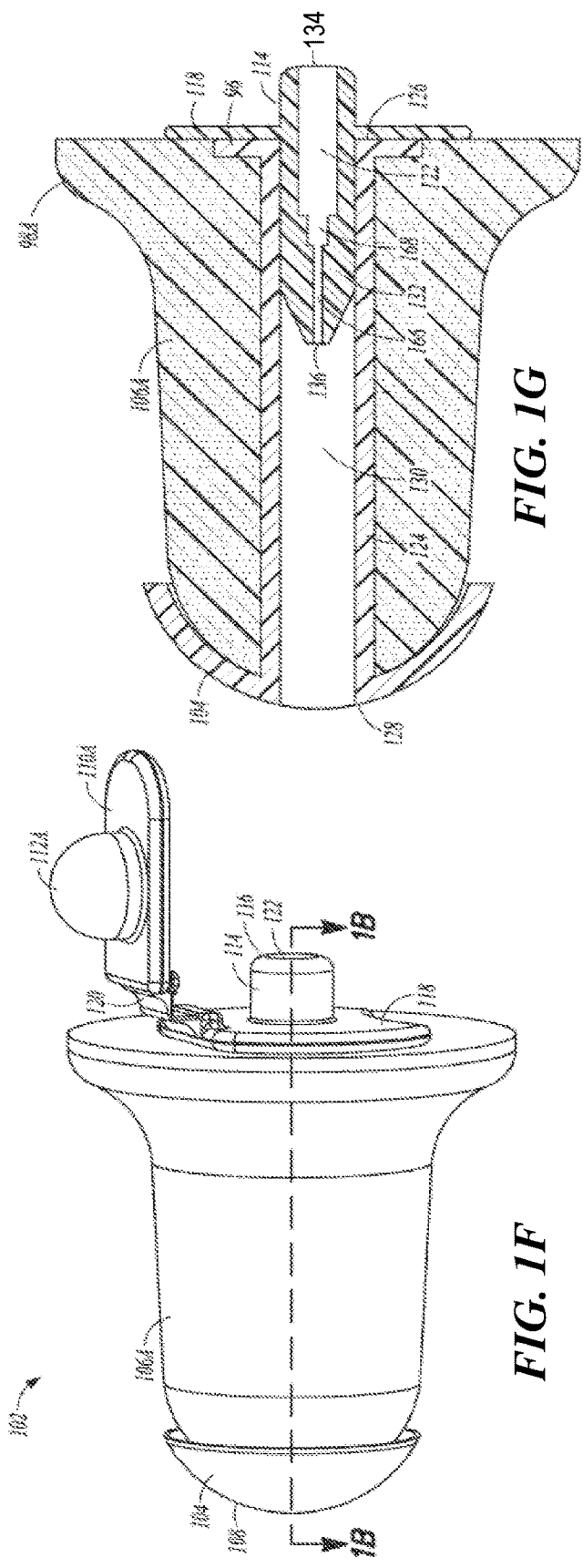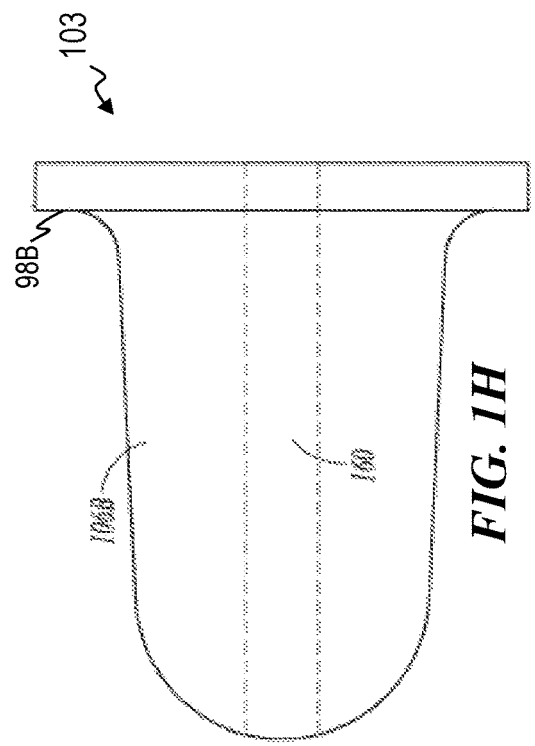

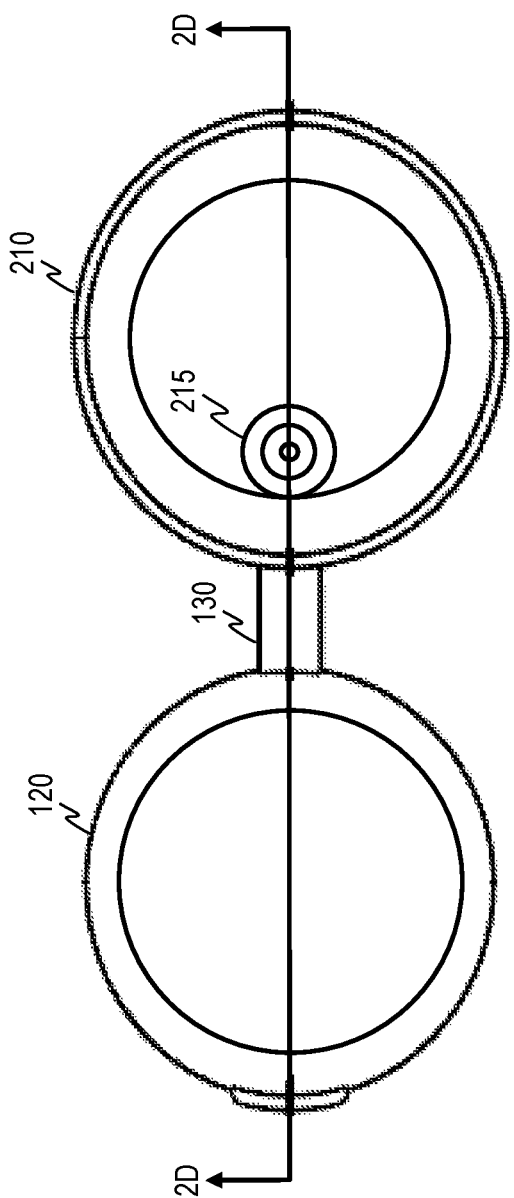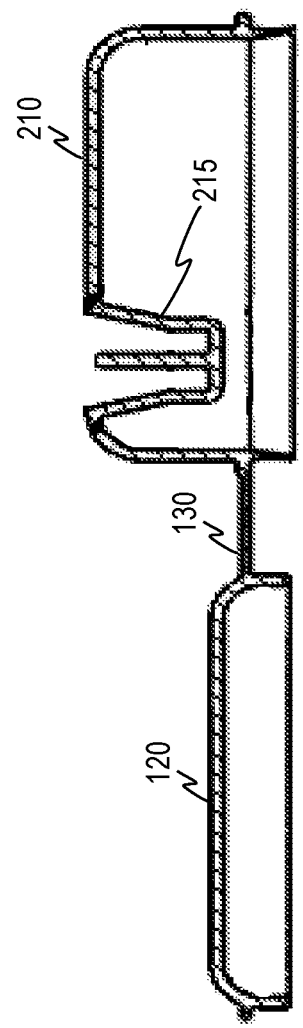
*FIG. 2C*
*FIG. 2D*

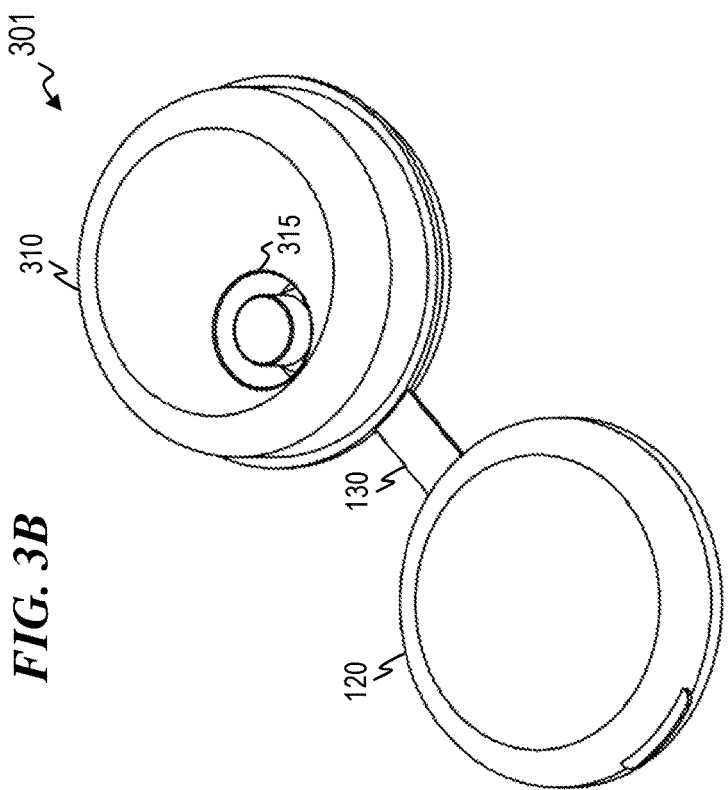
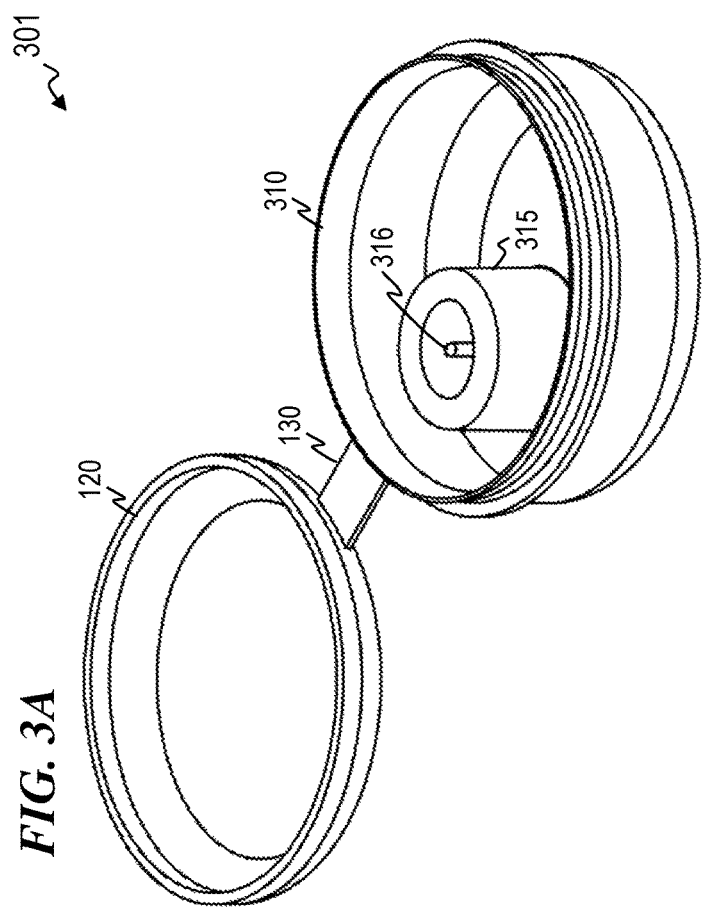
FIG. 3A
FIG. 3B

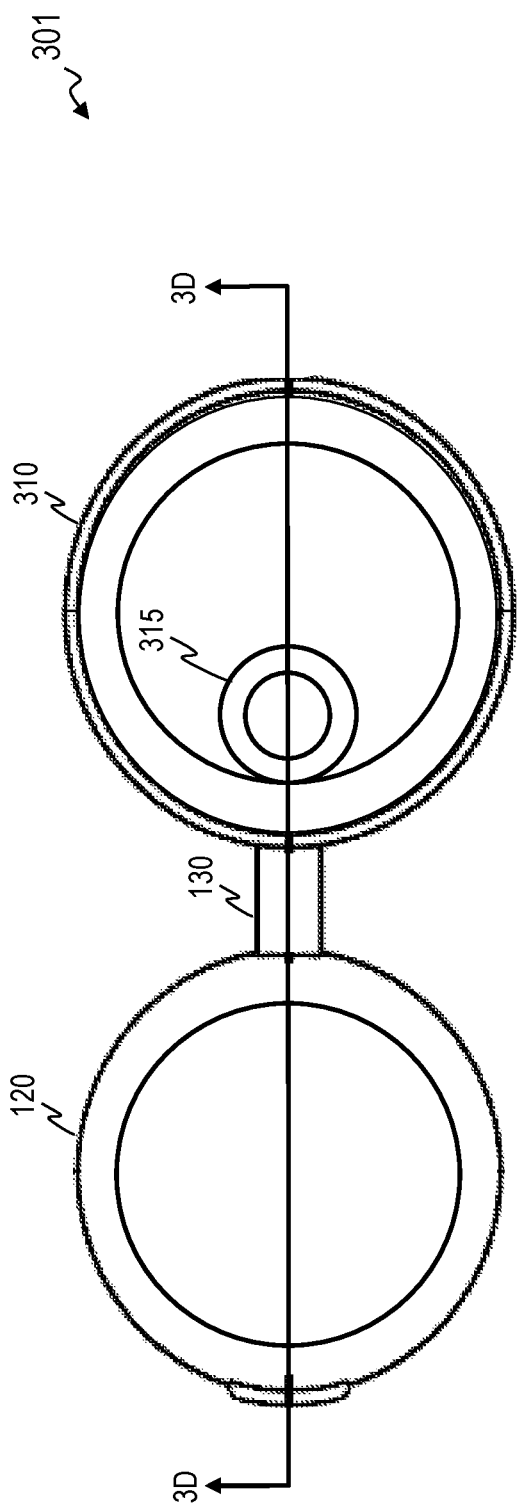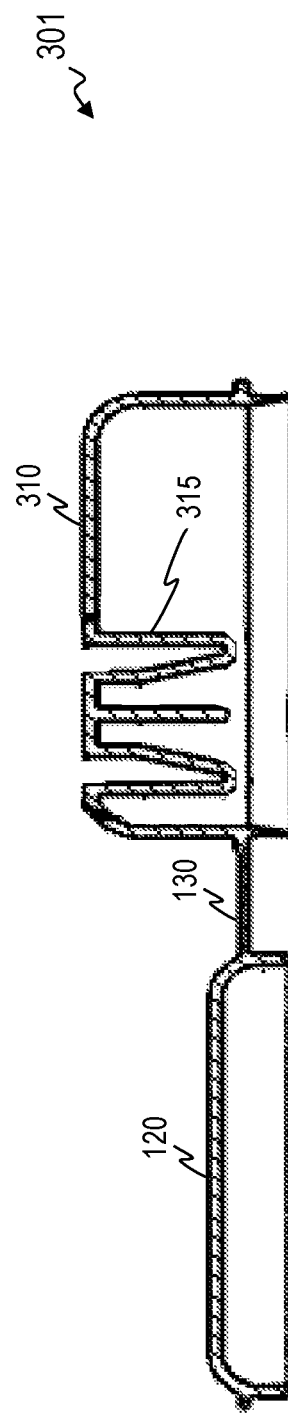
FIG. 3C
FIG. 3D

EARPIECE-FOAM SIZING APPARATUS AND METHOD

CROSS-REFERENCE TO RELATED APPLICATIONS

This application is a national-phase filing of, and claims priority benefit of, PCT Patent Application No. PCT/US2020/066494, filed Dec. 21, 2020 by David M. Chenal and titled "APPARATUS AND METHOD FOR AN EARPIECE-FOAM SHAPING/SIZING TOOL AND CONTAINER," which claims priority benefit, including under 35 U.S.C. § 119(e), of U.S. Provisional Patent Application 62/953,181 titled "APPARATUS AND METHOD FOR AN EARPIECE-FOAM SHAPING/SIZING TOOL AND CONTAINER," filed Dec. 23, 2019 by JMJ Holdings, LLC, each of which is incorporated herein by reference in its entirety.

This application is related to U.S. Design patent application Ser. No. 29/718,377, filed Dec. 23, 2019 by JMJ Holdings, LLC, titled "EARPIECE-FOAM SIZING TOOL" (which issued as U.S. Design Pat. No. D959,670 on Aug. 2, 2022), which is incorporated herein by reference in its entirety.

FIELD OF THE INVENTION

The present invention relates to devices and methods for shaping/sizing an earpiece foam part and optionally attaching the shaped part to an earphone or earplug piece and associated storage container, and in particular to a system and method for storing, sizing, and cleaning earphones and earplugs and the foam tips thereof.

BACKGROUND OF THE INVENTION

U.S. Pat. No. 7,236,605 by Robert J. Oliveira et al. issued on Jun. 26, 2007 with the title "User disposable sleeve for use within the ear canal", and is incorporated herein by reference. U.S. Pat. No. 7,236,605 describes user disposable sleeves for use with sound controlling structures having a non-constant radial profile that can include an inner portion adapted to releasably attach to the sound controlling structure and an outer portion adapted to fit within a user's ear canal. The user disposable sleeve can include holding means configured to releasably secure the sleeve to the elongate sound controlling structure and fitment means configured to conform to an inner surface of an ear. The fitment means can be fixedly disposed over the holding means.

U.S. Pat. No. 8,327,973 by William Parish et al. issued on Dec. 11, 2012 with the title "Foam compositions with enhanced sound attenuation", and is incorporated herein by reference. U.S. Pat. No. 8,327,973 describes foam compositions with enhanced sound attenuation characteristics for use in earpieces, for example, user-disposable foam members such as foam tips for sound control devices including sound transmission devices and earplugs in which a relationship between the size of the pores and the volume of the cells of the polymeric may be controlled.

U.S. Pat. No. 8,960,366 by Justin C. Peskar et al. issued on Feb. 24, 2015 with the title "Foam cushion for headphones", and is incorporated herein by reference. U.S. Pat. No. 8,960,366 describes a composite foam cushion for a sound control device. The cushion includes a core formed of a polymeric foam material and a polymeric coating overlying at least a portion of the core of polymeric foam material. The polymeric coating includes an outer coating layer and an inner polymeric coating layer bonded to the core of polymeric foam material. The inner coating layer may provide the cushion with strength, while providing a high degree of flexibility and suppleness to closely conform around contours and obstructions. The outer coating layer may provide the cushion with enhanced abrasion resistance and/or chemical resistance while having an aesthetically pleasing feel and appearance.

U.S. Pat. No. 9,092,965 by Christopher Thomas Lyons et al. issued on Jul. 28, 2015 with the title "System and method of detecting sleep disorders", and is incorporated herein by reference. U.S. Pat. No. 9,092,965 describes an apparatus for detecting sleep disorders, such as obstructive sleep apnea, includes a housing insertable into an ear canal of a subject. A sensor disposed within the housing measures a position of the subject's head relative to an axis of gravity. A transducer is responsive to the sensor and is capable of creating a stimulus detectable by the subject under certain conditions. In various embodiments, a controller receives signals corresponding to a pitch angle and a roll angle of the subject's head measured by the sensor, determines if the pitch and roll angles correspond to a sleep apnea inducing position, and causes the transducer to generate a stimulus upon determining that the subject's head is in the sleep apnea inducing position more than a predetermined threshold number of times. Various parameters of the stimulus may be modified with successive stimulus generation until a non-sleep apnea inducing position is detected.

U.S. Pat. No. 9,603,746 by David M. Chenal issued on Mar. 28, 2017 with the title "Sound attenuation", and is incorporated herein by reference. U.S. Pat. No. 9,603,746 describes a sound attenuation system that can include a first end that can include a shaft and a flange, the flange can be coupled to the shaft, and a second end that can include a filter stem and a cap. The filter stem can have a hole. The cap can have a first position in which the cap occludes the hole and can have a second position in which the cap is clear of the hole.

There remains a need for a shaping apparatus to cleanly shape foam earpieces for insertion into the ear canal, and for an all-in-one apparatus to store and shape/size foam earpieces.

SUMMARY OF THE INVENTION

The present invention provides an earpiece-foam shaping/sizing system that includes a bottom portion configured to store an earpiece, wherein the earpiece includes at least a foam portion, a cap configured to removably couple to the bottom portion; and a sizer configured to receive the foam portion in order to compress the foam portion such that the foam portion is configured to fit inside an ear of a user.

BRIEF DESCRIPTION OF THE FIGURES

FIG. 1F is a perspective diagram of an earplug 102, according to some embodiments of the present invention.

FIG. 1G is a cross-section view of earplug 102, according to some embodiments of the present invention.

FIG. 1H is a diagram of an earplug 103 having foam body 106B, according to some embodiments of the present invention.

FIG. 2C is a bottom-view diagram of earpiece-foam shaping system 201, according to some embodiments of the present invention.

FIG. 2D is a cross-section view of earpiece-foam shaping system 201, as viewed along the cross-section line shown in FIG. 2C, according to some embodiments of the present invention.

FIG. 3A is a top-view perspective diagram of an earpiece-foam shaping system 301, according to some embodiments of the present invention.

FIG. 3B is a bottom-view perspective diagram of earpiece-foam shaping system 301, according to some embodiments of the present invention.

FIG. 3C is a bottom-view diagram of earpiece-foam shaping system 301, according to some embodiments of the present invention.

FIG. 3D is a cross-section view of earpiece-foam shaping system 301, as viewed along the cross-section line shown in FIG. 3C, according to some embodiments of the present invention.

DETAILED DESCRIPTION OF THE INVENTION

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

Figure 1A:
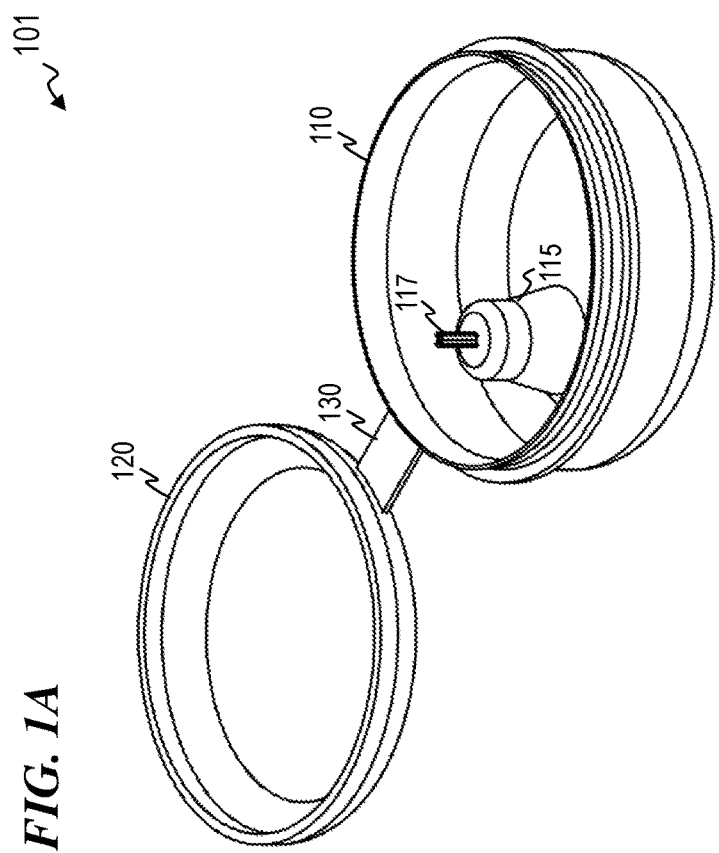
FIG. 1A is a top-view perspective diagram of an earpiece-foam shaping system 101, according to some embodiments of the present invention.

FIG. 1A is a top-view perspective diagram of an earpiece-foam shaping system 101, according to some embodiments of the present invention. In some embodiments, system 101 includes a bottom portion 110 and a cap 120. In some embodiments, bottom portion 110 has a hollow, cylindrical shape with an open top that allows one or more earpieces (e.g., earplugs, earphones, foam tips, or the like) to be placed into and stored in bottom portion 110. In some embodiments, cap 120 is configured to be removably coupled to a top section of bottom portion 110 such that the hollow area of bottom portion 110 is covered. In some embodiments, cap portion 120 snaps onto the top section of bottom portion 110, in some embodiments, cap portion 120 screws onto the top section of bottom portion 110, in some embodiments, cap portion 120 removably couples to the top section of bottom portion 110 in any other suitable manner. In some embodiments, even when cap 120 is removed from the top section of bottom portion 110, cap 120 remains connected to bottom portion 110 via a connection piece 130 (in some such embodiments, connection piece 130 ensures that cap 120 is always near bottom portion 110 in order to reduce the risk of losing cap 120 when it is not coupled to the top section of bottom portion 110). In some embodiments, connection piece 130 is a living hinge (i.e., a thin flexible hinge made from the same material as the two rigid pieces it connects).

In some embodiments, bottom portion 110 includes a hollow cone-shaped structure 115 (also referred to as a sizer or a sizer tool) that is open to the bottom outside surface of bottom portion 110 and is configured to receive an earpiece (or at least a portion of an earpiece such as a foam tip) such that at least a portion of the earpiece can be reduced in sized (e.g., compressed) before being placed into the ear (in some such embodiments, the user twists the earpiece into sizer 115 in order to compress the earpiece). In some embodiments, sizer tool 115 eliminates the need for a user to roll the foam (or other pliable material) portion of an earpiece between the fingers in order to compress the foam portion such that it fits inside the ear of the user (in some embodiments, rolling the foam portion of an earpiece between the fingers exposes the foam portion to dirt and other undesired matter). In some embodiments, at least a portion of the earpiece is made of a foam composition such as described in U.S. Pat. No. 8,327,973; in other embodiments, at least a portion of the earpiece is made of any other suitable pliable material that can be compressed by being placed into sizer 115. In some embodiments, having sizer tool 115 open to the bottom outside surface of bottom portion 110 allows a user to insert an earpiece into sizer tool 115 while keeping the hollow area of bottom portion 110 covered by cap 120 such that other earpieces stored in bottom portion 110 do not fall out of bottom portion 110 during use of sizer tool 115.

Figure 1B:
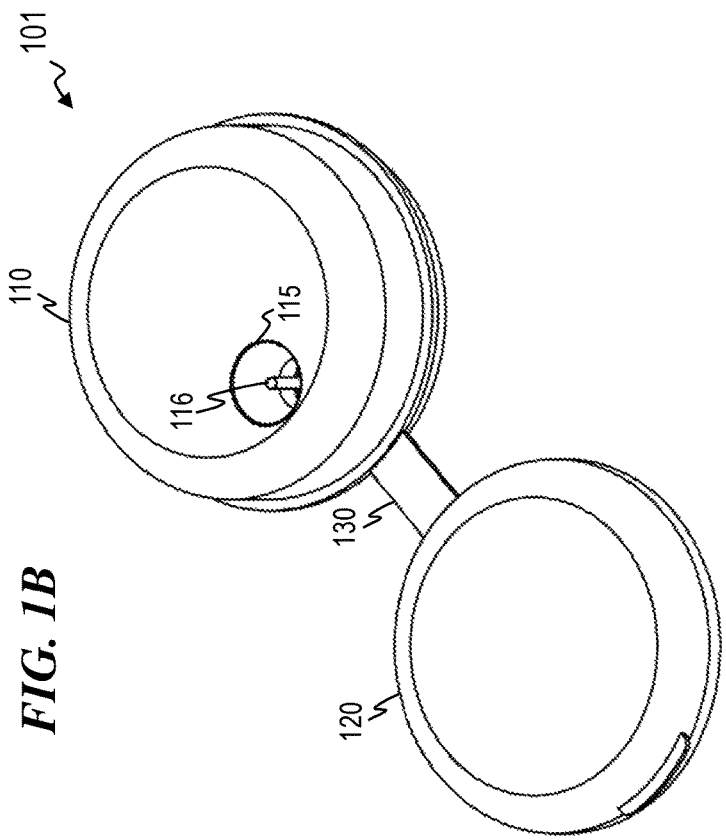
FIG. 1B is a bottom-view perspective diagram of earpiece-foam shaping system 101, according to some embodiments of the present invention.

FIG. 1B is a bottom-view perspective diagram of earpiece-foam shaping system 101, according to some embodiments of the present invention.

Figure 1C:
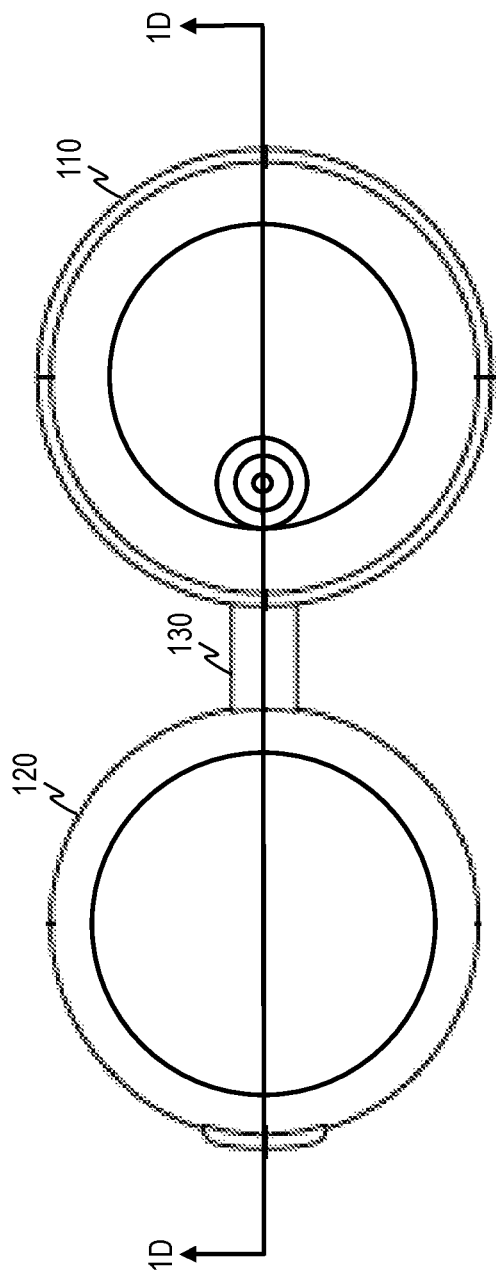
FIG. 1C is a bottom-view diagram of earpiece-foam shaping system 101, according to some embodiments of the present invention.

FIG. 1C is a bottom-view diagram of earpiece-foam shaping system 101, according to some embodiments of the present invention.

Figure 1D:
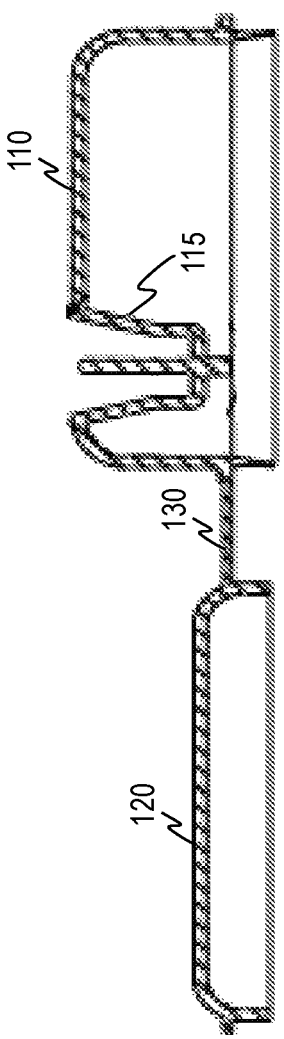
FIG. 1D is a cross-section view of earpiece-foam shaping system 101, as viewed along the cross-section line shown in FIG. 1C, according to some embodiments of the present invention.

FIG. 1D is a cross-section view of earpiece-foam shaping system 101, as viewed along the cross-section line shown in FIG. 1C, according to some embodiments of the present invention.

Figure 1E:
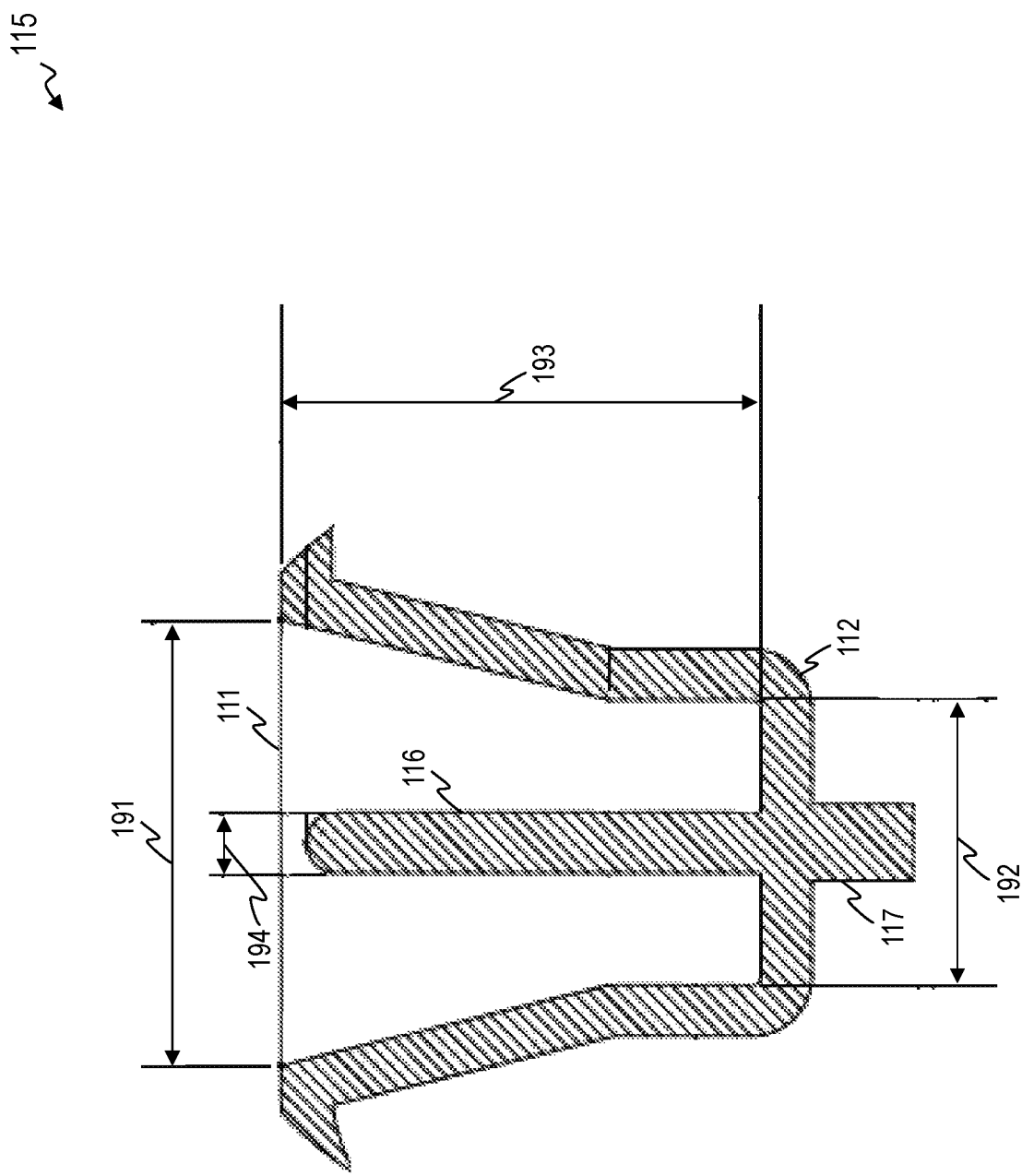
FIG. 1E is a cross-section view of sizer 115, according to some embodiments of the present invention.

FIG. 1E is a cross-section view of sizer 115, according to some embodiments of the present invention. In some embodiments, sizer 115 has a conical opening such that the cross-sectional area of sizer 115 is larger at the open end 111 of sizer 115 than at the closed end 112 of sizer 115 located in the interior of cap 110. For example, in some embodiments, open end 111 has a diameter 191 and closed end 112 has a diameter 192 that is smaller than diameter 191. In some embodiments, sizer 115 has a depth 193.

In some embodiments, sizer tool 115 includes a center post 116 that is configured to center the earpiece inside sizer tool 115 (in some such embodiments, center post 116 is further configured to prevent collapse of a center cavity of the earpiece during compression of the earpiece by sizer tool 115). In some embodiments, center post 116 has a diameter 194. In some embodiments, center post 116 extends past sizer 115 and into the hollow space of bottom portion 110 in order to provide a cleaning tool 117 for cleaning ear wax and other undesired material off of an earpiece. In some embodiments, sizer tool 115 is further configured to hold the foam portion of an earpiece stationary when the foam portion is placed in sizer tool 115 such that a barbed component (e.g., a barbed component of an earplug) can be threaded onto the foam portion while the foam portion is in sizer tool 115 (e.g., in some embodiments, sizer tool 115 includes barbs or ridges that are configured to hold the foam portion in place such as the barbs 618 shown in sizer 615 of FIG. 6A).

FIG. 1F is a perspective diagram of an exemplary earplug 102 (see, e.g., U.S. Pat. No. 9,603,746) that can be compressed using any of the sizer tools described herein, according to some embodiments of the present invention. Earplug 102 includes a first end 108 and a second end 116. Earplug 102 includes a flange 104, a foam body 106A, a cap 110A, a knob 112A, a port boss 114, a base plate 118, a joint 120, and a hole 122. Knob 112A is coupled to the cap 110A. Knob 112A helps the user to grasp the earplug 102.

FIG. 1G is a cross-section view of earplug 102, according to some embodiments of the present invention. Earplug 102 includes a tube (e.g., a shaft 124 having a bore 130). Shaft 124 includes a receiver end 126 and an emitter end 128. Bore 130 terminates at the receiver end 126 and at the emitter end 128. Flange 104 is coupled to the shaft 124. Earplug 102 includes a sound filter, a portion of which is illustrated in the figure. The sound filter includes a filter stem 132. Filter stem 132 includes an inlet end 134 and an outlet end 136. Filter stem 132 includes the hole 122. Hole 122 terminates at the inlet end 134 and at the outlet end 136. Hole 122 extends through the port boss 114. Hole 122 includes a first chamber 166 having a first diameter and a second chamber 168 having a second diameter. In the example of FIG. 1G, the first diameter is less than the second diameter. Filter stem 132 is configured to be at least partially inside of the bore 130. Outlet end 136 is configured to be inside the bore 130. In an example, the filter stem 132 has a press fit with the bore 130, such that filter stem 132 can expand the bore 130. As such, the press fit can use friction to secure the filter stem 132 in the bore 130. A portion of the filter stem 132 is tapered, such as at the outlet end 136 as shown in the example of FIG. 1G. The taper at the outlet end 136 can aid the insertion of the filter stem 132 into the bore 130 in the assembly of the earplug 102. Foam body 106A abuts the base plate 118.

In some examples, the first chamber 166 and second chamber 168 can be positioned, sized, or shaped in different configurations within the hole 122. The first diameter can be greater than the second diameter. The hole 122 can include one or more chambers (e.g., one, two, three, four, or more). In some embodiments, shaft 124 has a first elastic material having a first durometer. In one example, shaft 124 includes silicone. The filter stem 132 has a second elastic material. The second elastic material has a second durometer. The first durometer is less than the second durometer. A shape of the ear canal can be non-uniform along its length. Shaft 124 can bend when inserted into the ear canal. The first durometer is configured to allow the shaft 124 to conform to the shape of the ear canal. The second durometer is configured to have the filter stem 132 substantially retain its shape (e.g., the filter stem 132 is more rigid than the shaft 124). In one example, the base plate 118 has the second durometer. In one example, shaft 124 has a durometer of between 30 and 40 on the shore A scale. In one example, shaft 124 has a durometer of 35 on the shore A scale. Earplug 102 is inserted into an ear canal of a user to attenuate sound. The user holds the cap 110A of the earplug 102 for inserting the first end 108 into the ear canal. In an example, the user can hold the cap 110A between a finger and thumb. The user's finger can engage the knob 112A. The thumb can cover the cavity 138. A portion of the thumb can occlude the hole 122 during the insertion of the earplug 102 into the ear canal. In an example, the user presses the thumb onto a portion of the port boss 114 to occlude the hole 122. With the thumb occluding the hole 122, the user can hear that the earplug 102 is positioned at a location that attenuates sound. In some examples, the knob 112A has various shapes and sizes, for example—rounded, such as a hemisphere in the example of FIG. 1F. The knob 112A is a cylinder or a box according to some examples. The knob 112A can include multiple units, such as multiple bumps on a surface of the cap 110A configured to help the user grasp the earplug 102. Knob 112A can provide tactile feedback to aid the user in gripping and positioning earplug 102. In one example, knob 112A can provide a soft 'pop' that can be felt and heard when knob 112A is moved into a position to occlude the port boss. In some embodiments, knob 112A is optional. In various examples, an elbow component or interface device can engage with the port boss 114, with filter stem 132, or with bore 130 to allow attachment of a headset, a hearing aid, an interruptible foldback (IFB) device, or a telecommunications device. Base plate 118 is configured to maintain a position of the foam body 106A along the length of the shaft 124. Filter stem 132 is positioned inside the bore 130, such that the receiver end 126 is configured to abut the base plate 118. Flange 98A, in the example shown in FIG. 1G, has a radius on an inner edge. The outer edge is squared and, in some examples, provides a feature that can engage a prominence on the inner side of the ear anatomy and facilitate device retention. In some users, flange 98A engages the tragus or other anatomic feature, limiting depth of insertion of foam body 106A into the ear canal. In some configurations, flange 98A is fabricated of a material to mitigate or eliminate abrasion of skin surfaces proximate the foam body. Flange 98A can have a thin cross-section that is configured to deflect under a small force.

In one example, flange 96 is provided at an end of shaft 124. Flange 96 can facilitate retention of foam body 106A on shaft 124 or otherwise limit relative movement, in an axial direction, as to foam body 106A and shaft 124. In one example, flange 96 can be configured to provide a friction fit to retain a filter stem 132 or retain a headset, hearing aid, IFB, or telecommunications device. Flange 96 can take the form of a ring or a raised feature.

FIG. 1H is a diagram of an earplug 103 having foam body 106B, according to some embodiments of the present invention. Foam body 106B has a channel 160 extending through its center. Shaft 124 extends into the channel 160. A diameter of the channel 160 corresponds to an outer diameter of the shaft. In one example, the diameter of the channel 160 is less than the outer diameter of the shaft 124, such that the channel 160 is expanded from its resting state. In another example, the diameter of the channel 160 can be the same as or larger than the outer diameter of the shaft 124. In one example, the foam body 106B comprises "memory foam" such as polyurethane (PU). In various examples, foam body 106B is fabricated of polyvinyl chloride (PVC) or phthalate-free vinyl.

A shape of the foam body 106B has a larger outer diameter at one end, as shown in FIG. 1H. The size and shape of the foam body 106B is configured to fit inside the ear canal. Foam body 106B can have a compressed state or an expanded state. The foam body 106B can become compressed when the user presses the foam body 106B between two fingers, for example. Foam body 106B expands from the compressed state and returns to a natural configuration when the external compression is removed. In some embodiments, flange 98B is squared at both the inner edge and at the outer edge. Flange 98B can aid in device retention. In some examples, flange 98B can be positioned behind the tragus.

Foam body 106B abuts the inner concave surface of the flange 104, such as shown in the example of FIG. 1F. The user can compress the foam body 106B for easier insertion into the ear canal. The first end of the earplug 102 is inserted into the ear canal at a desired position. The flange 104 is configured to anchor (e.g., hold in place) the earplug 102. The foam body 106B can expand from the compressed state to engage the ear canal. The flange 104 anchors the earplug 102 in place by engaging the ear canal. The flange 104 has an outer surface (e.g., opposite the inner concave surface). The outer surface of the flange 104 presses against the ear canal having a diameter less than a flange diameter. A seal can be created by a component of the earplug 102 engaging (e.g., pressing against, held in place by friction, or touching) the ear canal.

In an example, the outer diameter of the shaft 124 can be different at the receiver end 126 and the emitter end 128 due to the taper of the shaft 124. In an example, the shaft 124 is configured to passively push (e.g., due to the taper) the foam body 106B toward the first end 108. The foam body 106B is passively pushed toward the flange 104. This enhances the first flange seal by encouraging the flange 104 to press into (e.g., expand into) the ear canal.

The first durometer allows the shaft 124 to bend to conform to a non-uniform shape of the ear canal. The foam body 106B is configured to support the shaft 124, such as to prevent the bore 130 from collapsing upon insertion of earplug 102 into the ear canal. As such, the foam body 106B can aid in preventing a blockage of sound through bore 130.

Figure 2B:
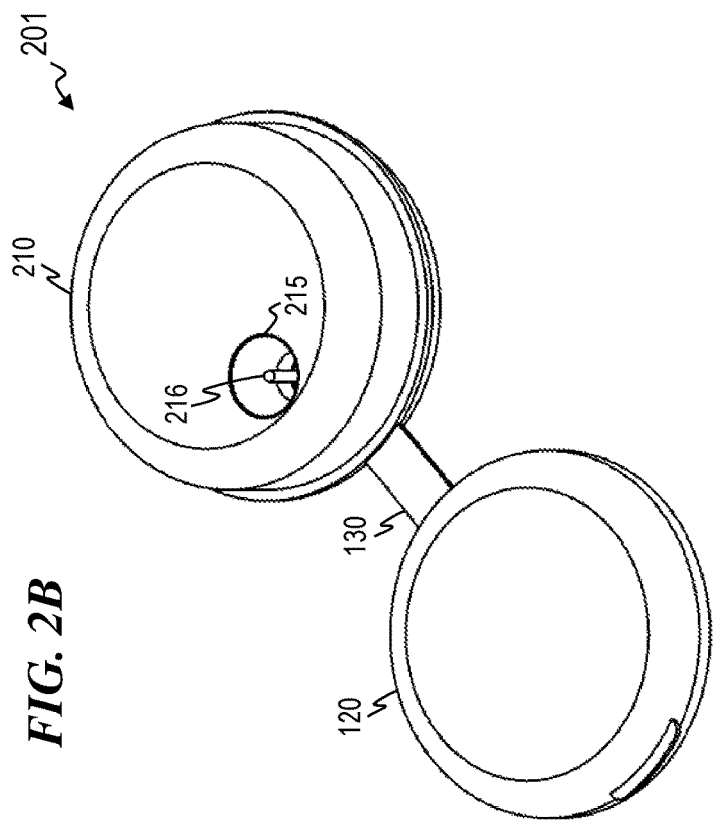
FIG. 2B is a bottom-view perspective diagram of earpiece-foam shaping system 201, according to some embodiments of the present invention.
Figure 2A:
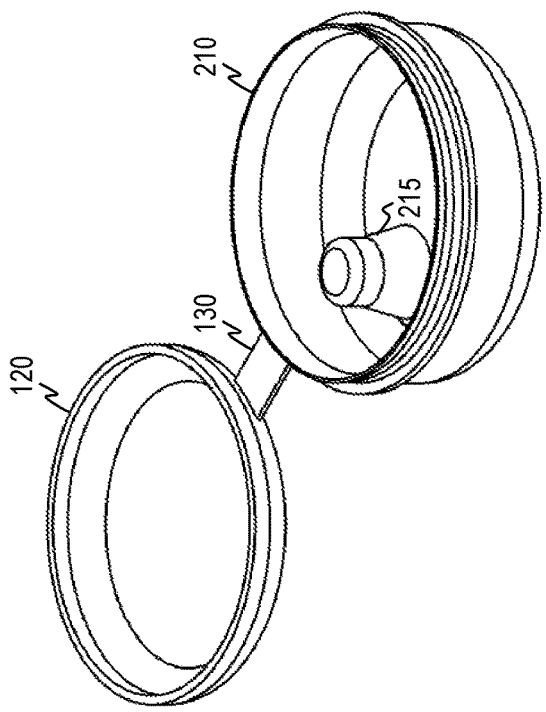
FIG. 2A is a top-view perspective diagram of an earpiece-foam shaping system 201, according to some embodiments of the present invention.

FIG. 2A is a top-view perspective diagram of an earpiece-foam shaping system 201, according to some embodiments of the present invention. In some embodiments, system 201 is substantially similar to system 101 except that bottom portion 110 is replaced by bottom portion 210 and sizer 115 is replaced by sizer 215.

FIG. 2B is a bottom-view perspective diagram of earpiece-foam shaping system 201, according to some embodiments of the present invention. In some embodiments, sizer 215 is substantially similar to sizer 115 (e.g., in some embodiments, sizer 215 includes a center post 216 similar to center post 116 of FIG. 1B) except that sizer 215 does not have a cleaning tool. In some embodiments, center post 216 has a diameter 294 (shown in FIG. 2E).

FIG. 2C is a bottom-view diagram of earpiece-foam shaping system 201, according to some embodiments of the present invention.

FIG. 2D is a cross-section view of earpiece-foam shaping system 201, as viewed along the cross-section line shown in FIG. 2C, according to some embodiments of the present invention.

Figure 2E:
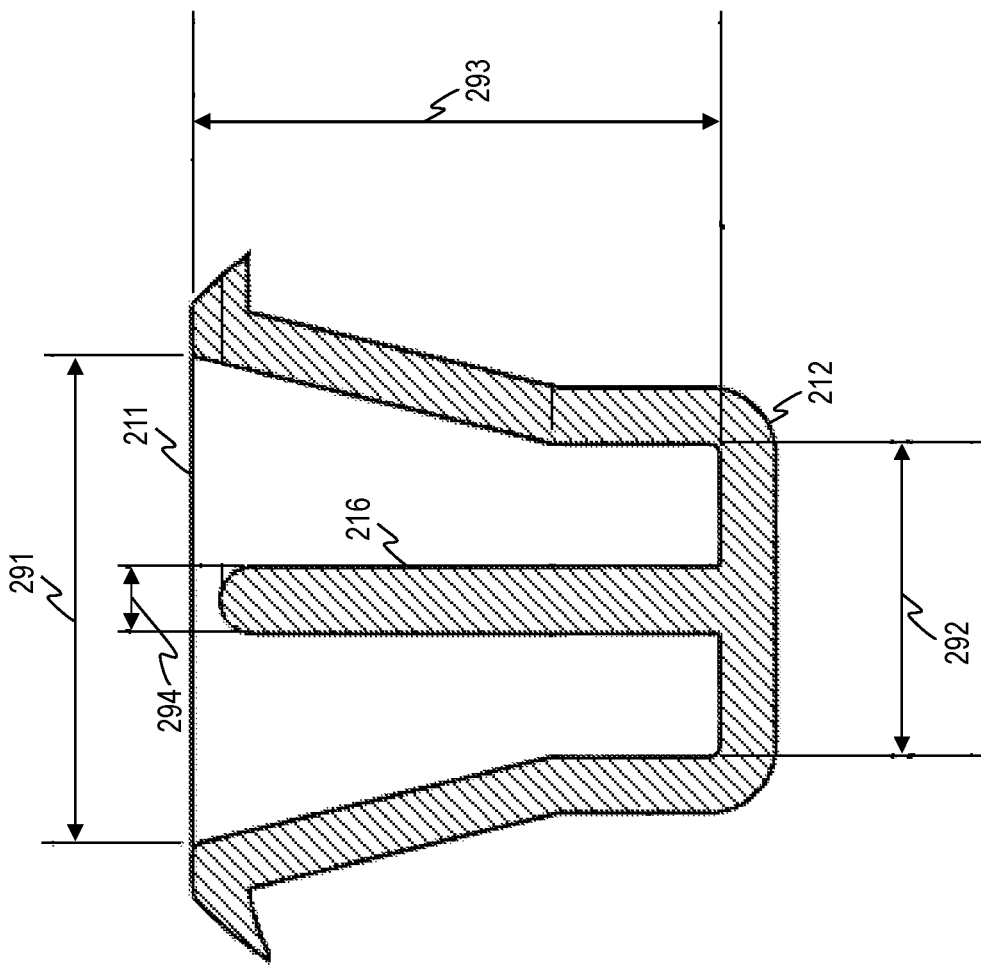
FIG. 2E is a cross-section view of sizer 215, according to some embodiments of the present invention.

FIG. 2E is a cross-section view of sizer 215, according to some embodiments of the present invention. In some embodiments, sizer 215 has a conical opening such that the cross-sectional area of sizer 215 is larger at the open end 211 of sizer 215 than at the closed end 212 of sizer 215 located in the interior of cap 110. For example, in some embodiments, open end 211 has a diameter 291 and closed end 212 has a diameter 292 that is smaller than diameter 291. In some embodiments, sizer 215 has a depth 293.

Figure 3E:
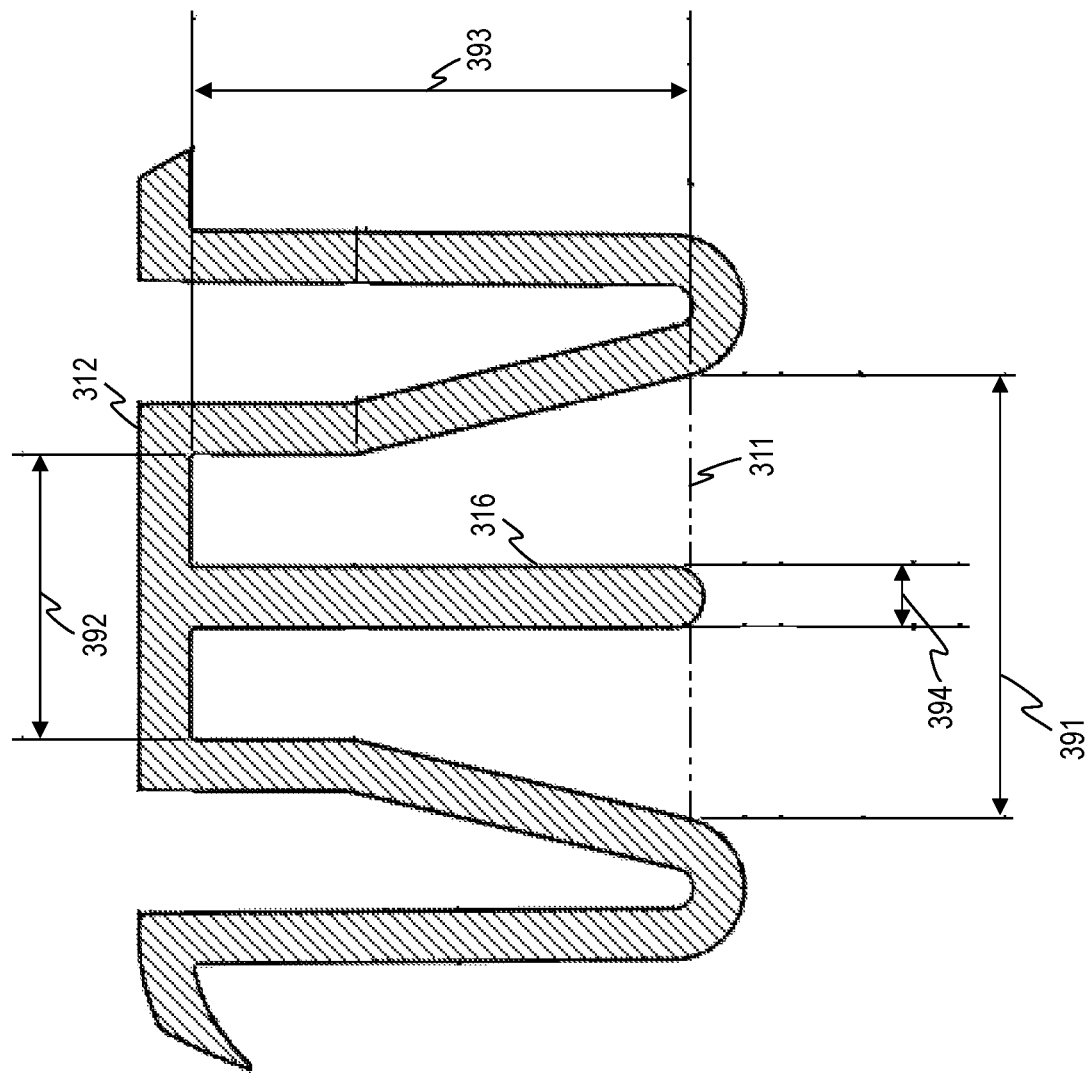
FIG. 3E is a cross-section view of sizer 315, according to some embodiments of the present invention.

FIG. 3A is a top-view perspective diagram of an earpiece-foam shaping system 301, according to some embodiments of the present invention. In some embodiments, system 301 is substantially similar to system 201 except that bottom portion 210 is replaced by bottom portion 310 and sizer 215 is replaced by sizer 315. In some embodiments, sizer 315 is substantially similar to sizer 215 except that sizer 315 is flipped around such that the opening of sizer 315 configured to receive the earpiece opens into the hollow area of bottom portion 310. In some such embodiments, sizer 315 includes a center post 316 that is substantially similar to center post 216 of FIG. 2B. In some embodiments, center post 316 has a diameter 394 (see FIG. 3E). In some embodiments, having sizer 315 open into the hollow area of bottom portion 310 prevents sizer 315 from collecting dirt and other unwanted material while sizer 315 is not in use.

FIG. 3B is a bottom-view perspective diagram of earpiece-foam shaping system 301, according to some embodiments of the present invention.

FIG. 3C is a bottom-view diagram of earpiece-foam shaping system 301, according to some embodiments of the present invention.

FIG. 3D is a cross-section view of earpiece-foam shaping system 301, as viewed along the cross-section line shown in FIG. 3C, according to some embodiments of the present invention.

FIG. 3E is a cross-section view of sizer 315, according to some embodiments of the present invention. In some embodiments, sizer 315 has a conical opening such that the cross-sectional area of sizer 315 is larger at the open end 311 of sizer 315 than at the closed end 312 of sizer 315 located toward the outside surface of bottom portion 310. For example, in some embodiments, open end 311 has a diameter 391 and closed end 312 has a diameter 392 that is smaller than diameter 391. In some embodiments, sizer 315 has a depth 393.

Figure 4A:
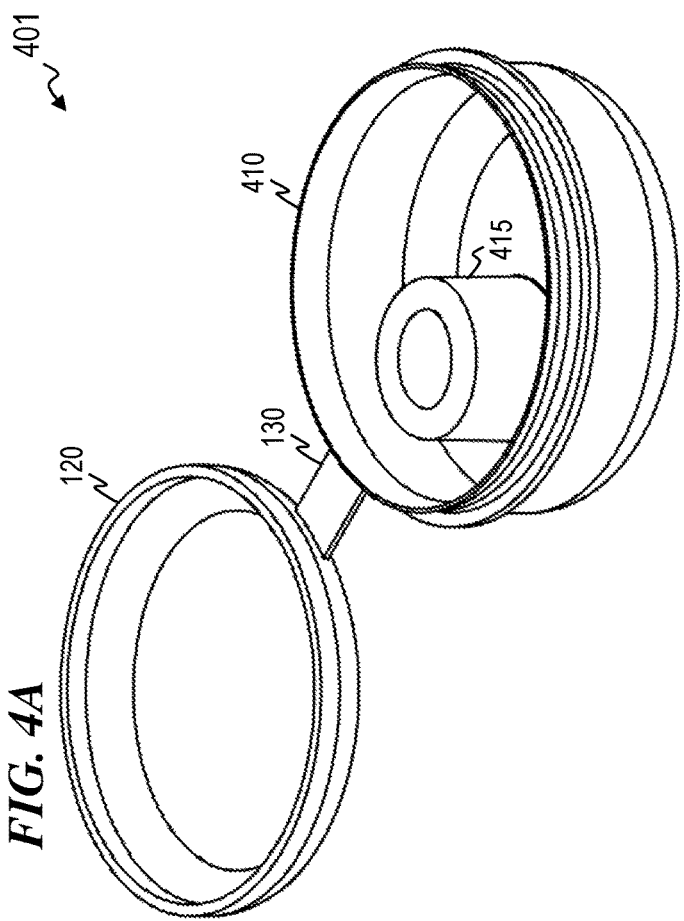
FIG. 4A is a top-view perspective diagram of an earpiece-foam shaping system 401, according to some embodiments of the present invention.

FIG. 4A is a top-view perspective diagram of an earpiece-foam shaping system 401, according to some embodiments of the present invention. In some embodiments, system 401 is substantially similar to system 301 except that bottom portion 310 is replaced by bottom portion 410 and sizer 315 is replaced by sizer 415. In some embodiments, sizer 415 is substantially similar to sizer 315 except that sizer 415 does not have a center post.

Figure 4B:
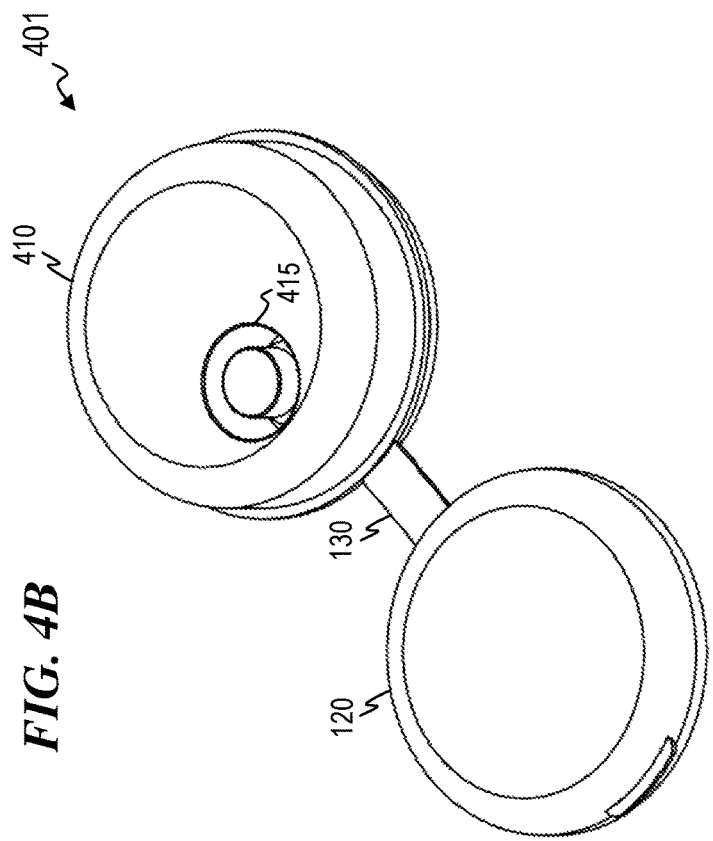
FIG. 4B is a bottom-view perspective diagram of earpiece-foam shaping system 401, according to some embodiments of the present invention.

FIG. 4B is a bottom-view perspective diagram of earpiece-foam shaping system 401, according to some embodiments of the present invention.

Figure 4C:
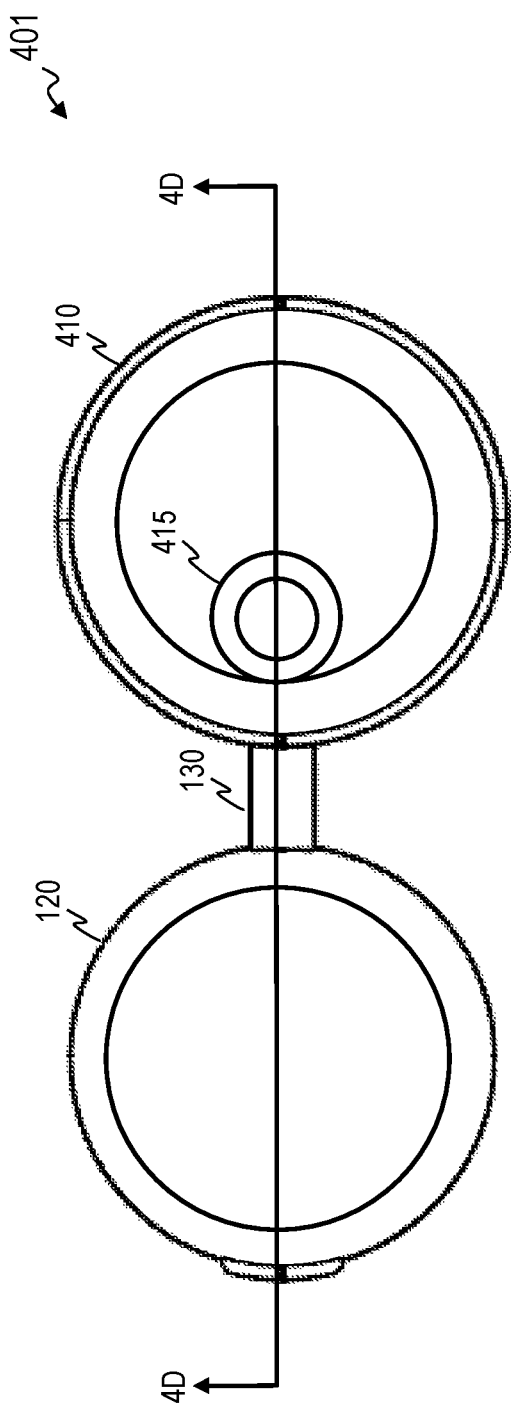
FIG. 4C is a bottom-view diagram of earpiece-foam shaping system 401, according to some embodiments of the present invention.

FIG. 4C is a bottom-view diagram of earpiece-foam shaping system 401, according to some embodiments of the present invention.

Figure 4D:
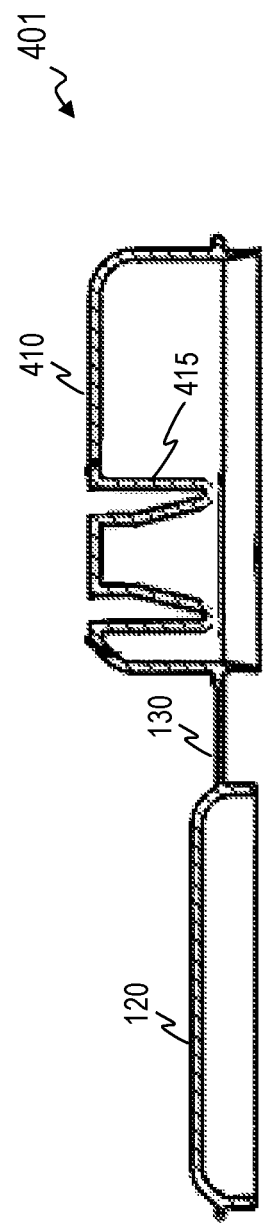
FIG. 4D is a cross-section view of earpiece-foam shaping system 401, as viewed along the cross-section line shown in FIG. 4C, according to some embodiments of the present invention.

FIG. 4D is a cross-section view of earpiece-foam shaping system 401, as viewed along the cross-section line shown in FIG. 4C, according to some embodiments of the present invention.

Figure 4E:
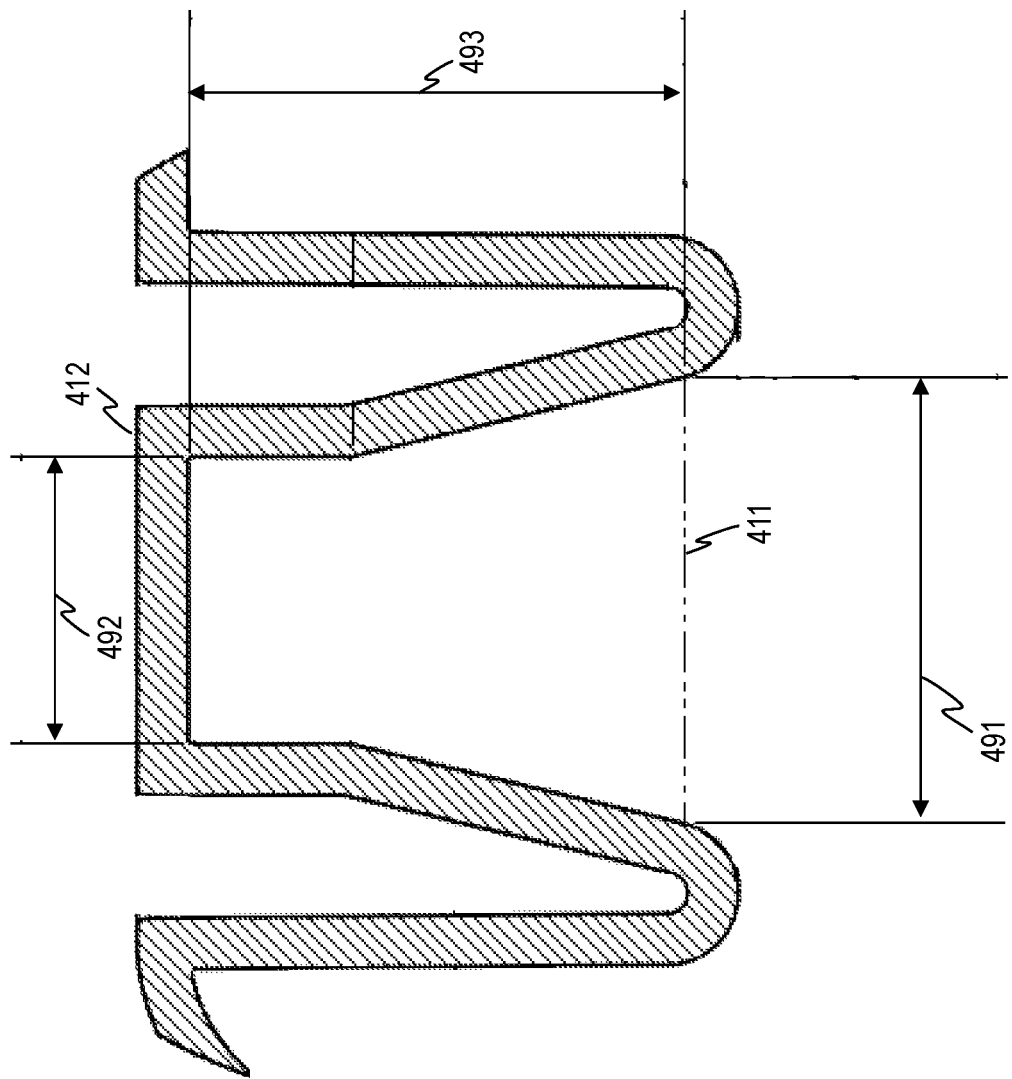
FIG. 4E is a cross-section view of sizer 415, according to some embodiments of the present invention.

FIG. 4E is a cross-section view of sizer 415, according to some embodiments of the present invention. In some embodiments, sizer 415 has a conical opening such that the cross-sectional area of sizer 415 is larger at the open end 411 of sizer 415 than at the closed end 412 of sizer 415 located toward the outside surface of bottom portion 410. For example, in some embodiments, open end 411 has a diameter 491 and closed end 412 has a diameter 492 that is smaller than diameter 491. In some embodiments, sizer 415 has a depth 493.

Figure 5B:
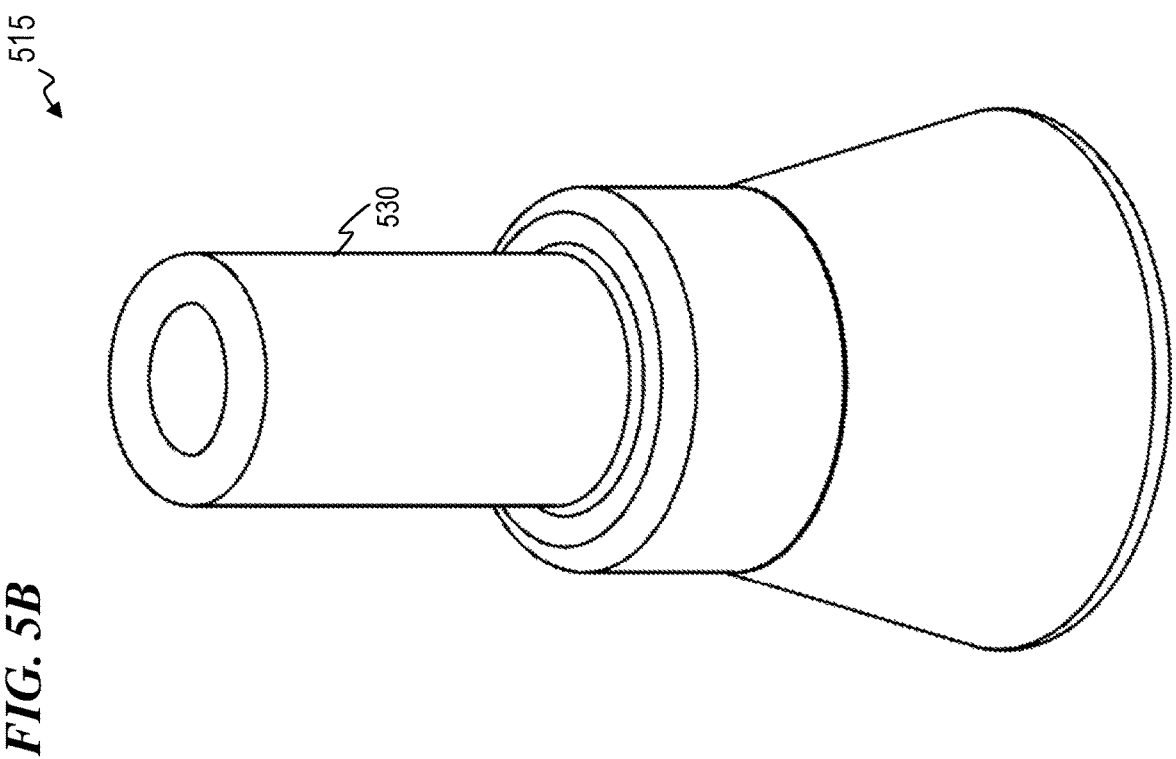
FIG. 5B is a bottom perspective view of sizer 515, according to some embodiments of the present invention.
Figure 5A:
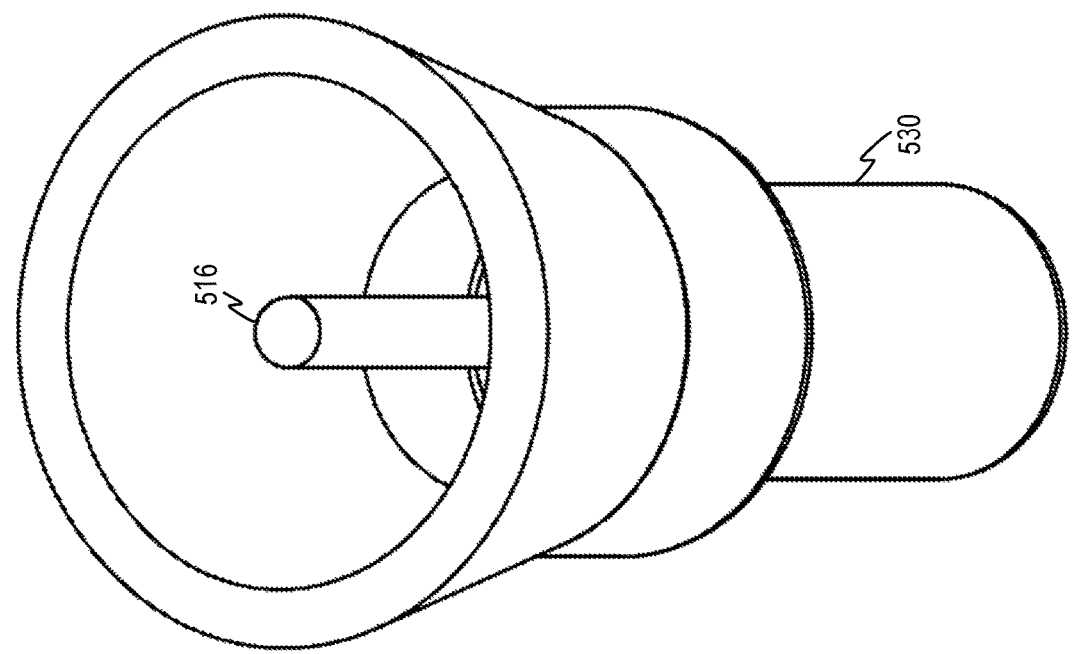
FIG. 5A is a top perspective view of a sizer 515, according to some embodiments of the present invention.

FIG. 5A is a top perspective view of a sizer 515, according to some embodiments of the present invention. In some embodiments, sizer 515 includes a center post 516 that is substantially similar to center post 216 of FIG. 2B. In some embodiments, sizer 515, like sizers 115, 215, 315, and 415, is configured to receive an earpiece (or at least a portion of an earpiece such as a foam tip) such that at least a portion of the earpiece can be reduced in sized (e.g., compressed) before being placed into the ear (in some such embodiments, the user twists the earpiece into sizer 515 in order to compress the earpiece). In some such embodiments, sizer 515 is a stand-alone device that is not integrated with the cap or bottom portion of an earpiece-foam shaping system described herein, but instead is configured to be stored in a bottom portion described herein with the earpiece(s). In some embodiments, sizer 515 includes a handle 530 for holding sizer 515.

FIG. 5B is a bottom perspective view of sizer 515, according to some embodiments of the present invention.

Figure 5C:
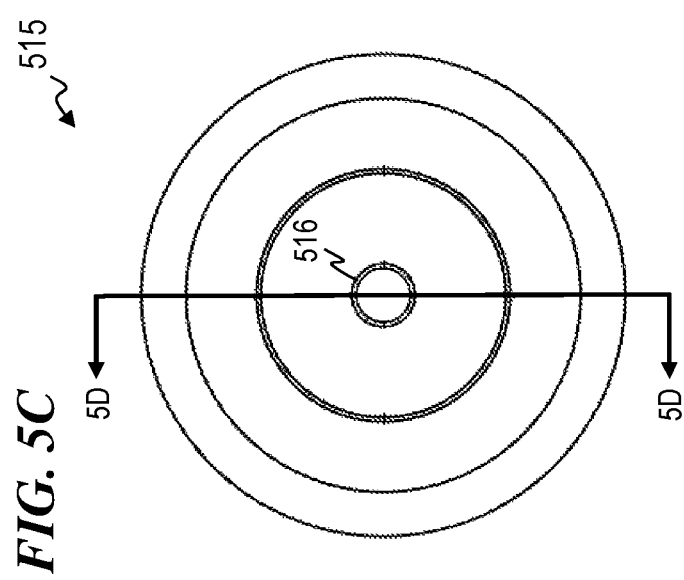
FIG. 5C is a top view of sizer 515, according to some embodiments of the present invention.

FIG. 5C is a top view of sizer 515, according to some embodiments of the present invention.

Figure 5D:
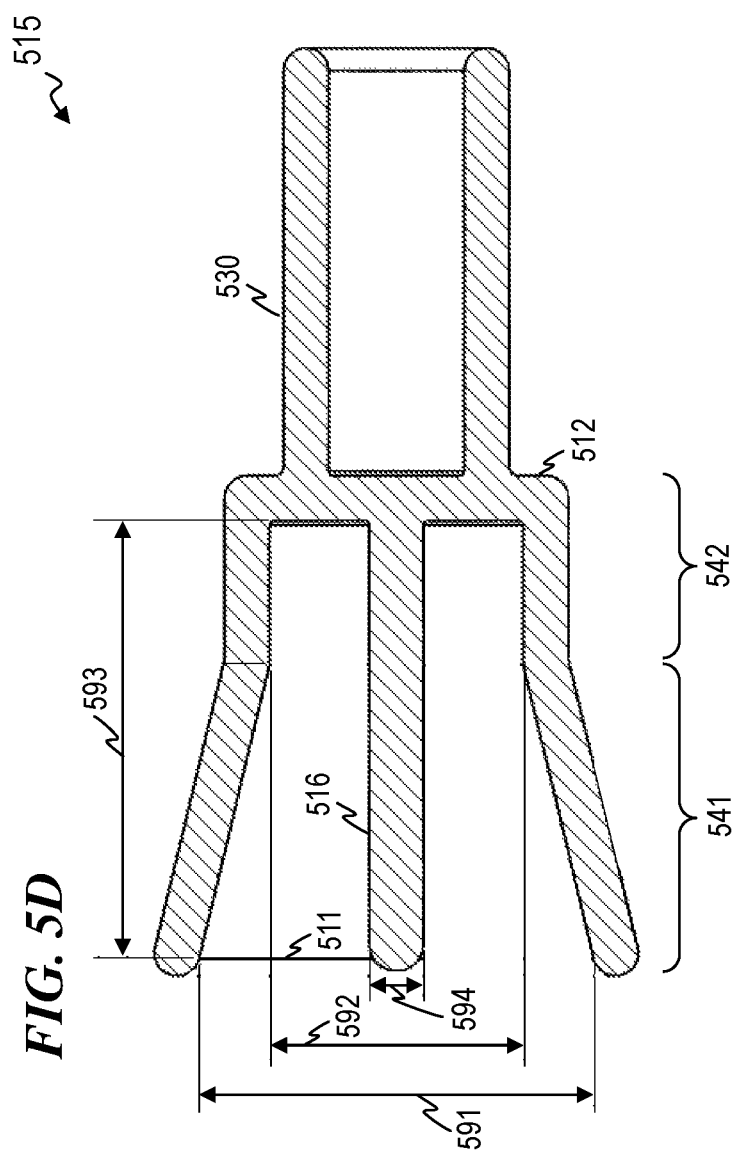
FIG. 5D is a cross-section view of sizer 515, as viewed along the cross-section line shown in FIG. 5C, according to some embodiments of the present invention.

FIG. 5D is a cross-section view of sizer 515, as viewed along the cross-section line shown in FIG. 5C, according to some embodiments of the present invention. In some embodiments, sizer 515 has a conical opening such that the cross-sectional area of sizer 515 is larger at the open end 511 of sizer 515 than at the closed end 512 of sizer 515. For example, in some embodiments, open end 511 has a diameter 591 and closed end 512 has a diameter 592 that is smaller than diameter 591. In some embodiments, sizer 515 has a depth 593 and center post 516 has a diameter 594. In some embodiments, sizer 515 includes a conical portion 541 closer to open end 511 and a cylindrical portion 542 closer to second end 512.

Figure 6B:
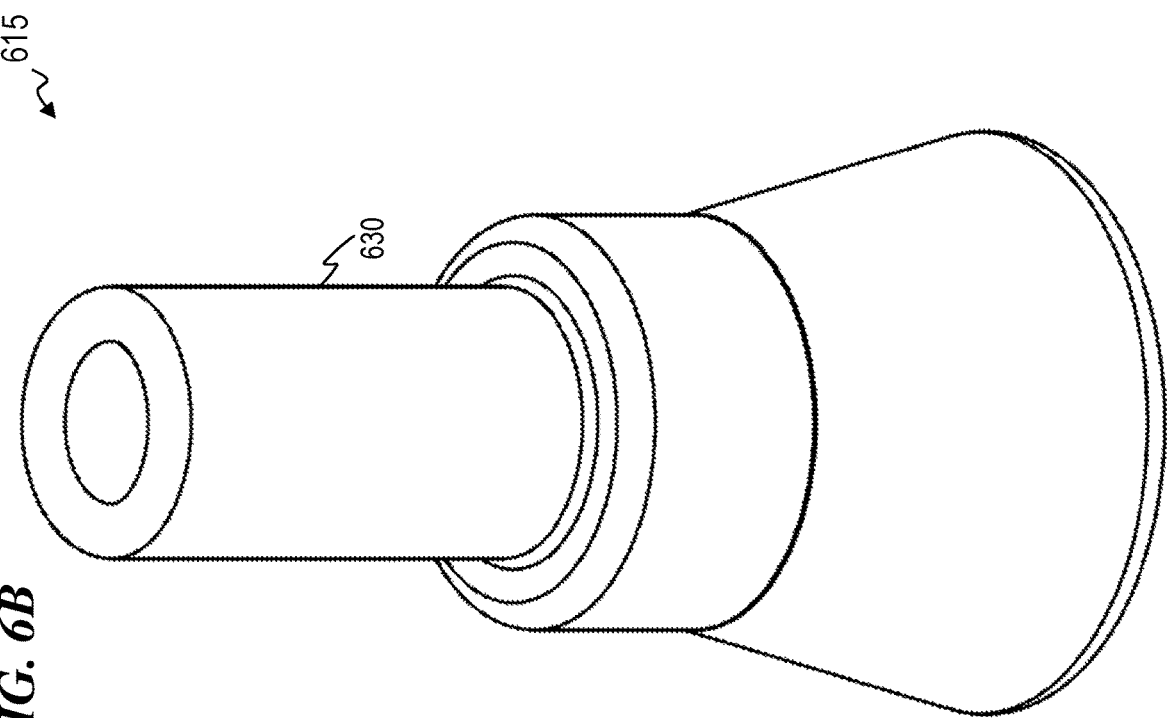
FIG. 6B is a bottom perspective view of sizer 615, according to some embodiments of the present invention.
Figure 6A:
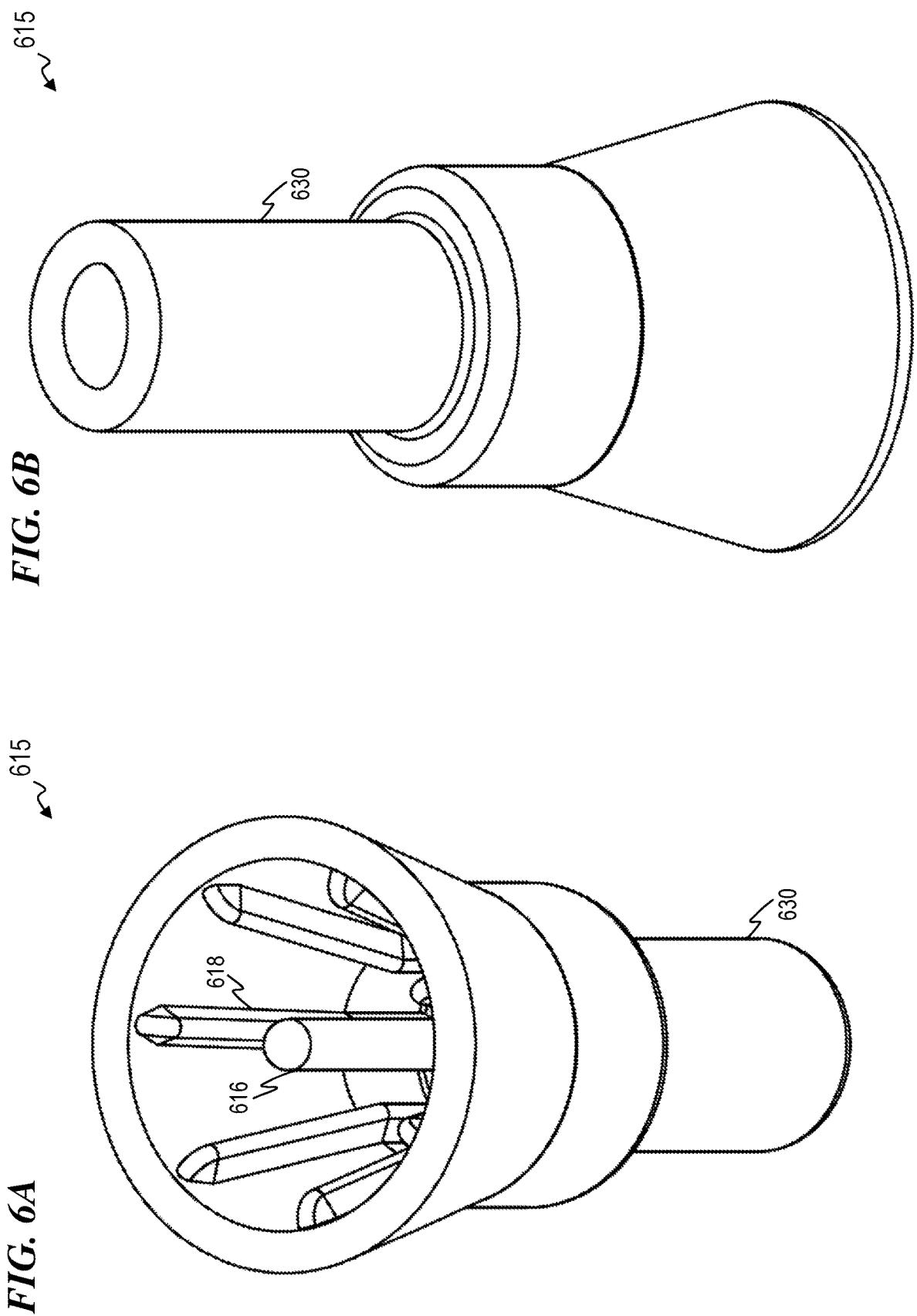
FIG. 6A is a top perspective view of a sizer 615, according to some embodiments of the present invention.

FIG. 6A is a top perspective view of a sizer 615, according to some embodiments of the present invention. In some embodiments, sizer 615 includes a center post 616 that is substantially similar to center post 216 of FIG. 2B. In some embodiments, sizer 615, like sizers 115, 215, 315, 415, and 515, is configured to receive an earpiece (or at least a portion of an earpiece such as a foam tip) such that at least a portion of the earpiece can be reduced in sized (e.g., compressed) before being placed into the ear. In some such embodiments, sizer 615 is a stand-alone device that is not integrated with the cap or bottom portion of an earpiece-foam shaping system described herein, but instead is configured to be stored in a bottom portion described herein with the earpiece(s). In some embodiments, sizer 615 includes one or more barbs or ridges 618 that are configured to hold the foam portion of an earpiece in place (e.g., prevent the foam portion from slipping) while the foam portion is inserted into sizer 615. In some embodiments, barbs 618 are configured to form corresponding grooves in the foam portion of the earpiece. In some embodiments, sizer 615 includes a handle 630 for holding sizer 615.

FIG. 6B is a bottom perspective view of sizer 615, according to some embodiments of the present invention.

Figure 6D:
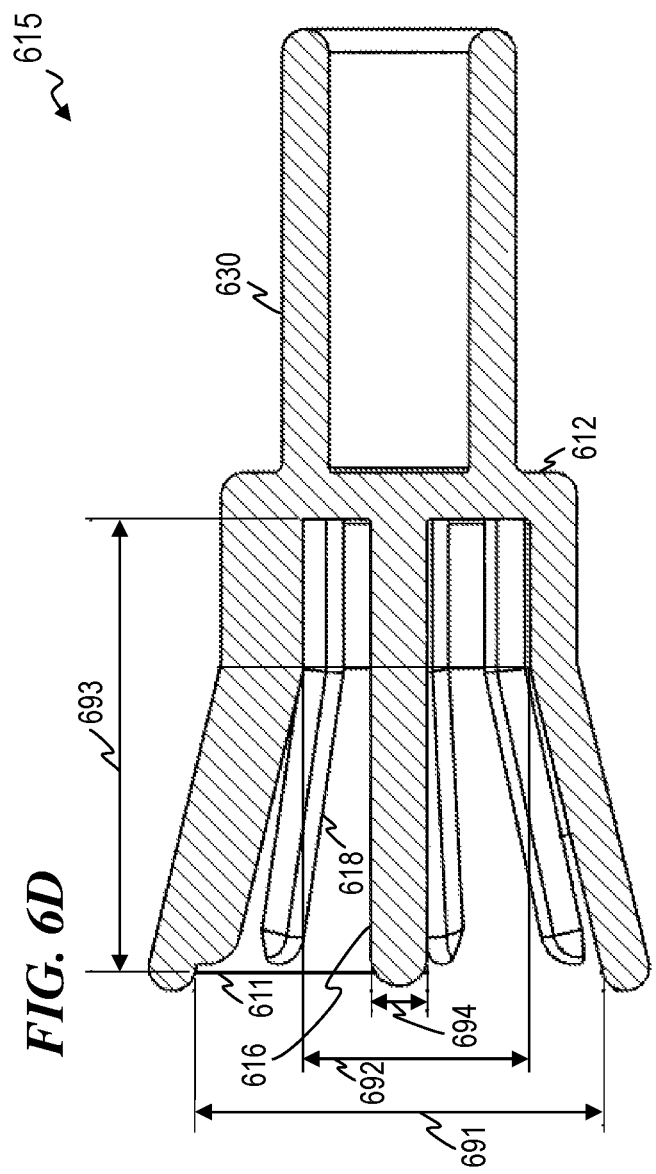
FIG. 6D is a cross-section view of sizer 615, as viewed along the cross-section line shown in FIG. 6C, according to some embodiments of the present invention.
Figure 6C:
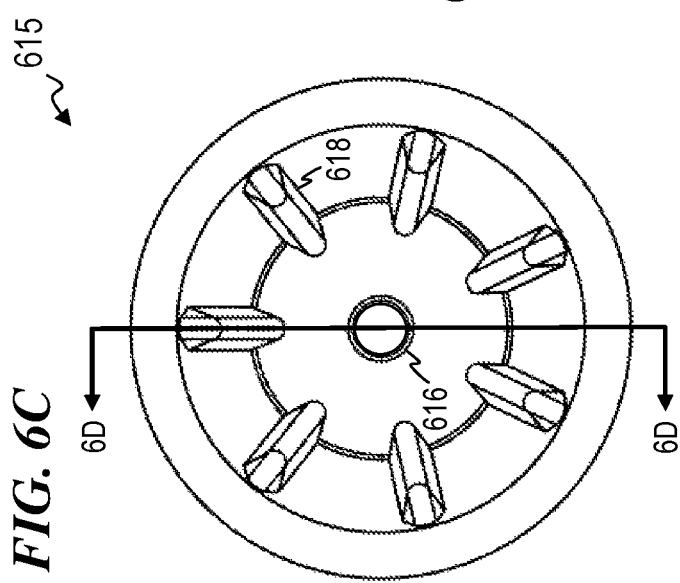
FIG. 6C is a top view of sizer 615, according to some embodiments of the present invention.

FIG. 6C is a top view of sizer 615, according to some embodiments of the present invention.

FIG. 6D is a view, partially in cross-section, of sizer 615, as viewed along the cross-section line shown in FIG. 6C, according to some embodiments of the present invention. In some embodiments, sizer 615 has a conical opening such that the cross-sectional area of sizer 615 is larger at the open end 611 of sizer 615 than at the closed end 612 of sizer 615. For example, in some embodiments, open end 611 has a diameter 691 and closed end 612 has a diameter 692 that is smaller than diameter 691. In some embodiments, sizer 615 has a depth 693 and center post 616 has a diameter 694.

Figure 7B:
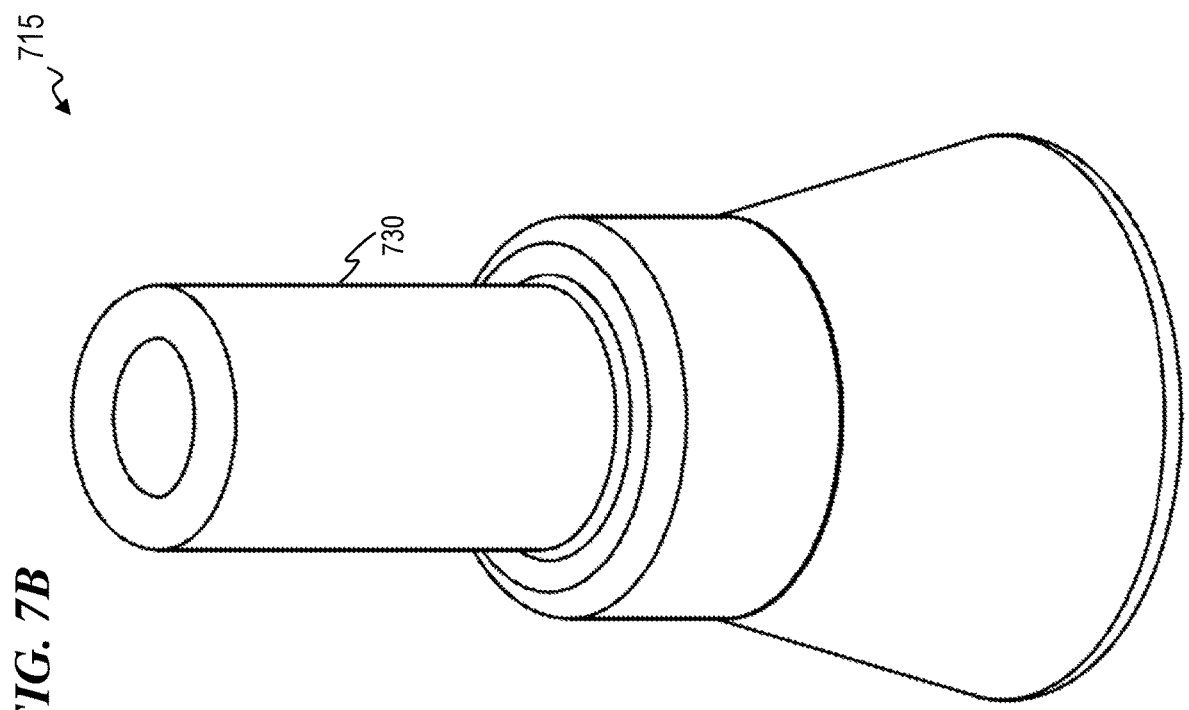
FIG. 7B is a bottom perspective view of sizer 715, according to some embodiments of the present invention.
Figure 7A:
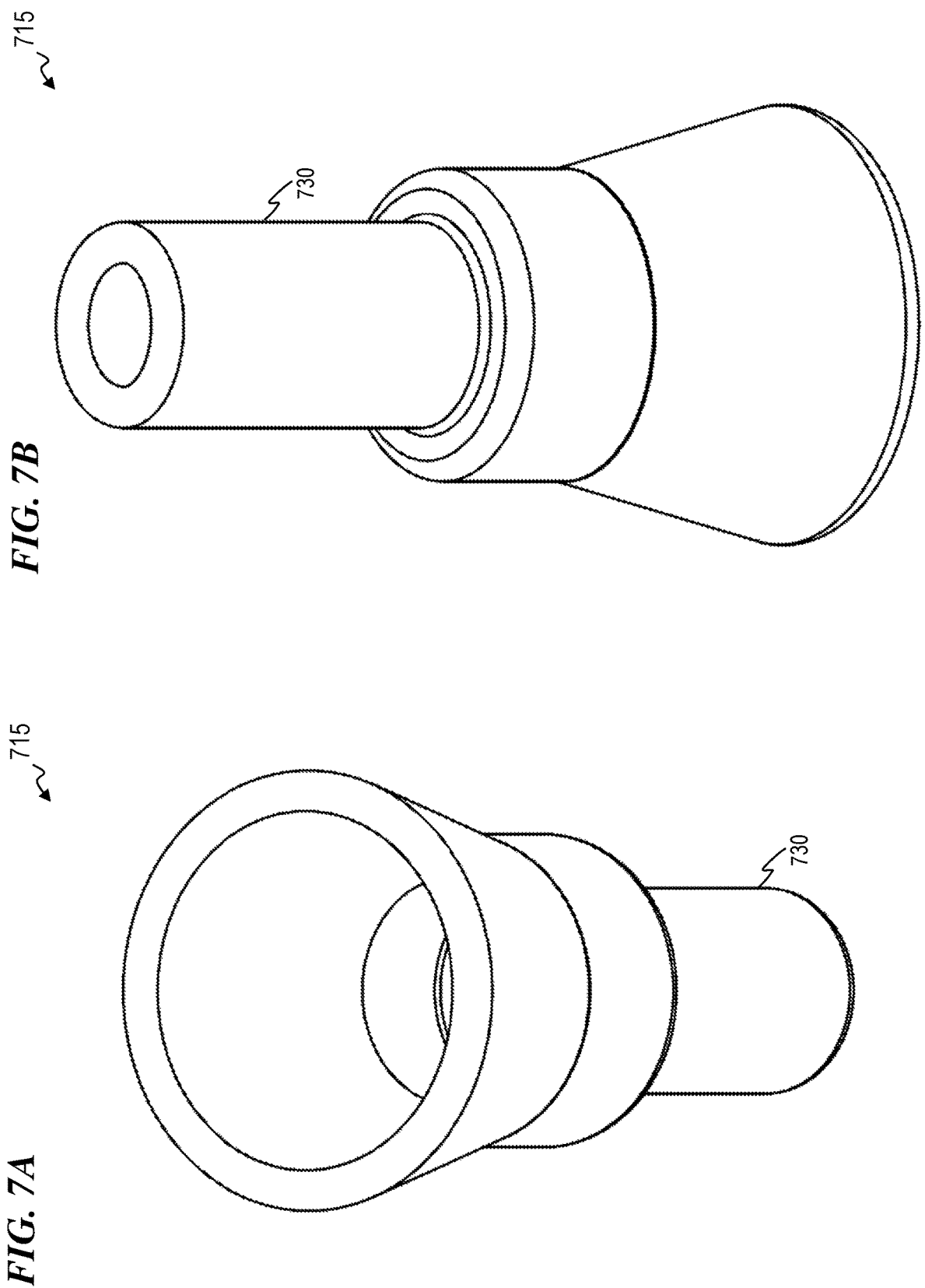
FIG. 7A is a top perspective view of a sizer 715, according to some embodiments of the present invention.

FIG. 7A is a top perspective view of a sizer 715, according to some embodiments of the present invention. In some embodiments, sizer 715, like sizers 115, 215, 315, 415, 515, and 615, is configured to receive an earpiece (or at least a portion of an earpiece such as a foam tip) such that at least a portion of the earpiece can be reduced in sized (e.g., compressed) before being placed into the ear. In some such embodiments, sizer 715 is a stand-alone device that is not integrated with the cap or bottom portion of an earpiece-foam shaping system described herein, but instead is configured to be stored in a bottom portion described herein with the earpiece(s). In some embodiments, sizer 715 is substantially similar to sizer 515 except that sizer 715 does not have a center post. In some embodiments, sizer 715 includes a handle 730 for holding sizer 715.

FIG. 7B is a bottom perspective view of sizer 715, according to some embodiments of the present invention.

Figure 7D:
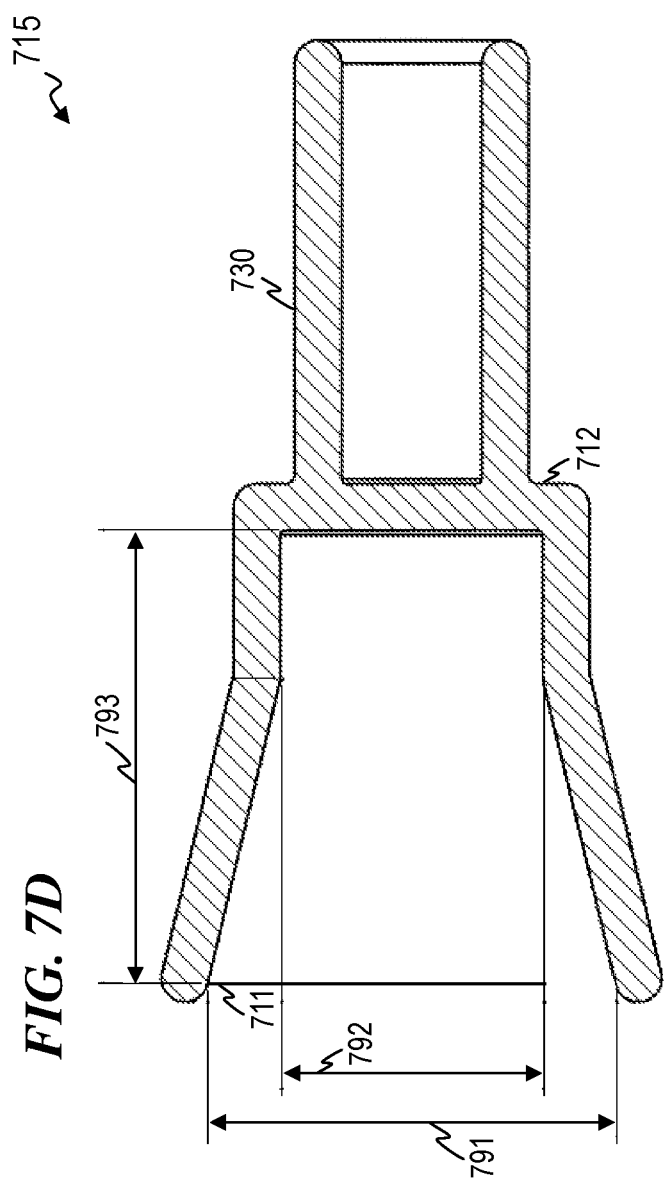
FIG. 7D is a cross-section view of sizer 715, as viewed along the cross-section line shown in FIG. 7C, according to some embodiments of the present invention.
Figure 7C:
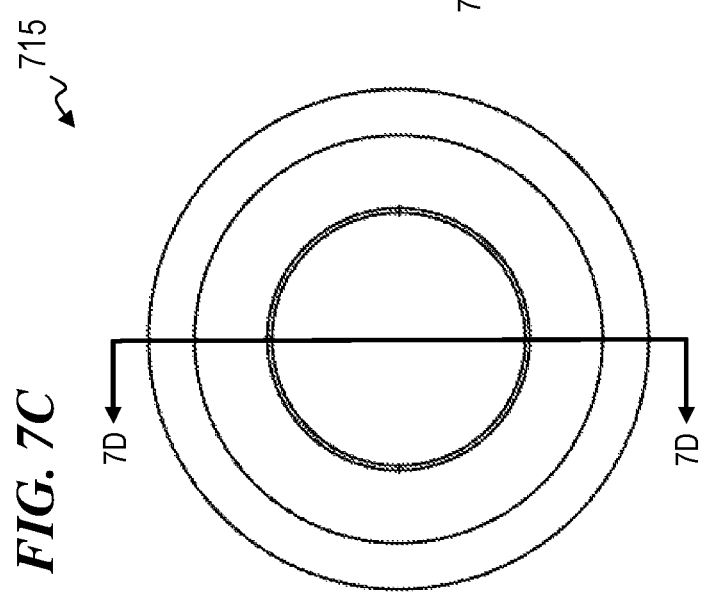
FIG. 7C is a top view of sizer 715, according to some embodiments of the present invention.

FIG. 7C is a top view of sizer 715, according to some embodiments of the present invention.

FIG. 7D is a cross-section view of sizer 715, as viewed along the cross-section line shown in FIG. 7C, according to some embodiments of the present invention. In some embodiments, sizer 715 has a conical opening such that the cross-sectional area of sizer 715 is larger at the open end 711 of sizer 715 than at the closed end 712 of sizer 715. For example, in some embodiments, open end 711 has a diameter 791 and closed end 712 has a diameter 792 that is smaller than diameter 791. In some embodiments, sizer 715 has a depth 793.

Figure 8:
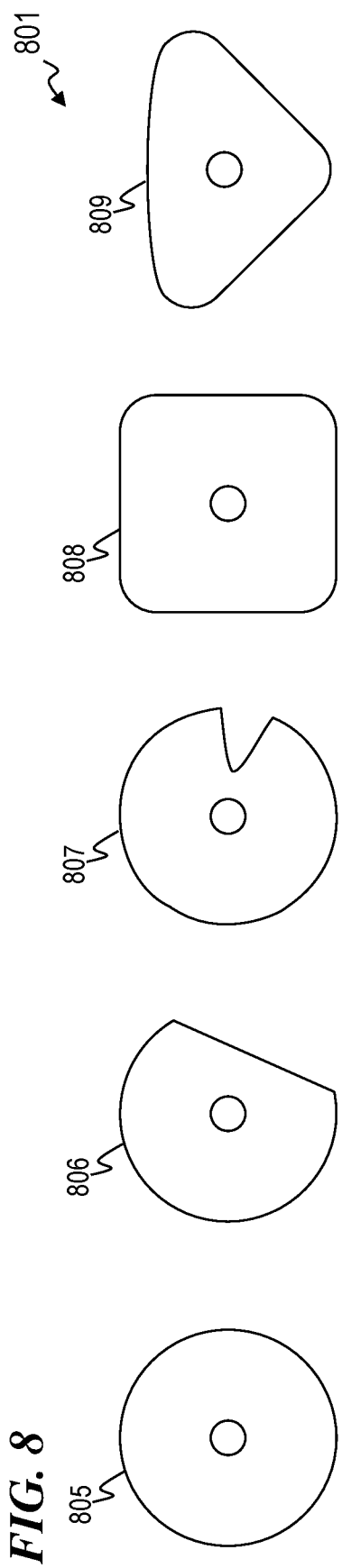
FIG. 8 is a schematic diagram showing a plurality of sizer-opening cross sections 801, according to some embodiments of the present invention.

FIG. 8 is a schematic diagram showing a plurality of sizer-opening cross sections 801, according to some embodiments of the present invention. In some embodiments, cross-sections 801 include sizer opening 805, sizer opening 806, sizer opening 807, sizer opening 808, and sizer opening 809. In some embodiments, any of the sizers described herein (e.g., sizer 115, 215, 315, 415, 515, 615, and 715) can be configured to include any one of the sizer-opening cross sections 801 shown in FIG. 8. In some embodiments, some of the cross sections 801 include notches or corners in the perimeter of the cross section that are configured to hold the foam portion of the earpiece in place while the earpiece is in the corresponding sizer (see, e.g., cross-sections 806, 807, 808, and 809). Cross section 805 represents a top view of a conical opening that has a center post, and is circularly symmetric. Cross section 806 is substantially similarly to cross-section 805, but includes one flat side, to prevent slipping of the foam upon twisting an earphone or earplug insert that is being inserted into the foam. Cross section 807 is substantially similarly to cross-section 805, but includes a single ridge, to prevent slipping of the foam upon twisting an earphone or earplug insert that is being inserted into the foam. Other embodiments include a plurality of barbs or ridges 618, such as shown in FIGS. 6A, 6C, and 6D. Cross section 808 represents a top view of a pyramidal opening that has a center post. Cross section 808 represents a top view of a tapered triangular opening that has a center post. Each of the embodiments illustrated in FIG. 8, except for 805, helps prevent sliding or rotating of the foam when the center insert is inserted. Other embodiments of the invention, similar to those of FIG. 8, omit the center post.

Figure 9:
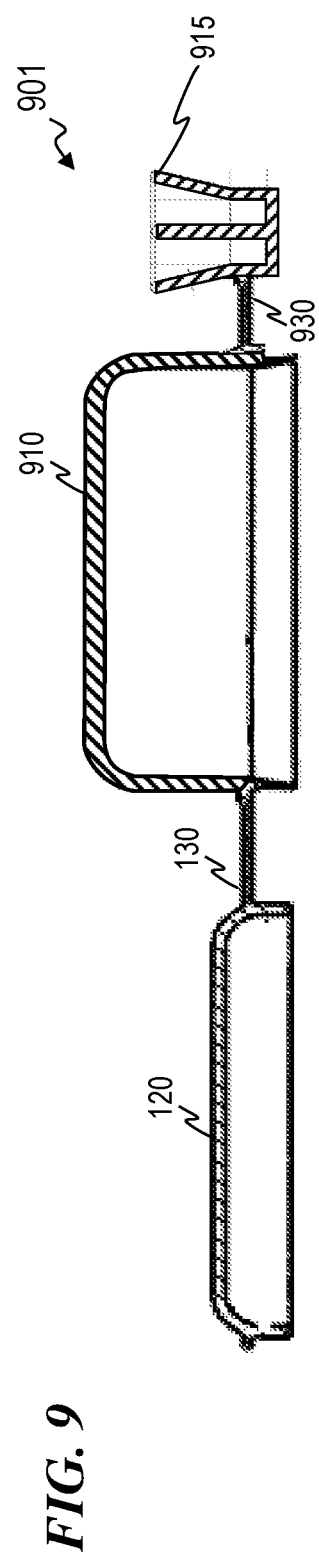
FIG. 9 is a cross-section view of an earpiece-foam shaping system 901, according to some embodiments of the present invention.

FIG. 9 is a cross-section view of an earpiece-foam shaping system 901, according to some embodiments of the present invention. In some embodiments, system 901 includes a sizer 915 that is not part of bottom portion 910, but rather is coupled to the exterior of bottom portion 910 via connection piece 930.

Figure 10:
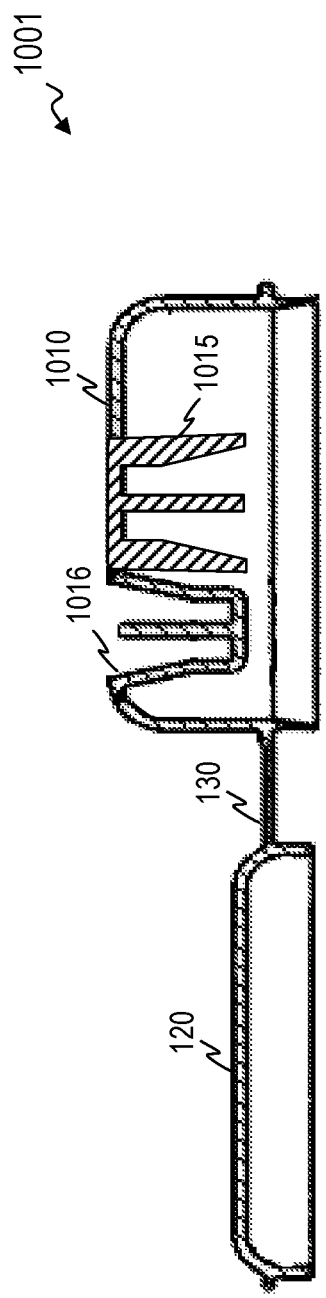
FIG. 10 is a cross-section view of an earpiece-foam shaping system 1001, according to some embodiments of the present invention.

FIG. 10 is a cross-section view of an earpiece-foam shaping system 1001, according to some embodiments of the present invention. In some embodiments, system 1001 includes two sizers, 1015 and 1016, that are both part of bottom portion 1010, but with one (sizer 1016) facing outward to be used with the case closed, and sizer 1015 facing inward to be used with the case open.

In some embodiments, the present invention provides an earpiece-foam shaping system that includes a container, wherein the container includes a cap, a bottom portion, and a sizer, wherein the sizer is integrated into the interior surface of the cap, rather than being integrated with the bottom portion or being a stand-alone device.

In some embodiments, the present invention provides an earpiece-foam shaping system that includes a bottom portion configured to store an earpiece, wherein the earpiece includes at least a foam portion, a cap configured to removably couple to the bottom portion; and a sizer configured to receive the foam portion in order to compress the foam portion such that the foam portion is configured to fit inside an ear of a user.

In some embodiments, the present invention provides a system for shaping at least a foam portion of an earpiece, the system including a sizer configured to receive at least the foam portion of the earpiece such that at least the foam portion of the earpiece is reduced in size before being placed into an ear of a user, wherein the sizer includes a hollow structure having an open first end and a second end, wherein the first end has a first cross-sectional area, wherein the second end has a second cross-sectional area, and wherein the first cross-sectional area is larger than the second cross-sectional area. In some embodiments, the hollow structure includes a conical portion closer to the first end and a cylindrical portion closer to the second end. In some embodiments, the second end is closed.

In some embodiments of the system, the sizer further includes a handle that extends from the second end of the hollow structure on a side of the second end opposite the open first end, and wherein the handle is configured to provide a grip for the user to hold the sizer as a stand-alone device. In some embodiments, the sizer further includes a center post that extends from the second end of the hollow structure toward the open first end of the hollow structure, wherein the center post is configured to keep the at least foam portion of the earpiece centered in the hollow structure. In some embodiments, the sizer further includes a cleaning tool coupled to the second end of the hollow structure on a side of the second end opposite the open first end (in some embodiments, the cleaning tool is an extension of the center post that extends in the opposite direction as the center post), and wherein the cleaning tool is configured to remove undesired material off of the earpiece. In some embodiments, the sizer further includes a plurality of barbs or ridges located along an interior surface of the hollow structure, wherein the plurality of barbs/ridges is configured to hold the at least foam portion of the earpiece in place while the at least foam portion is inserted into the sizer. In some embodiments, the plurality of ridges is configured to form further-compressed grooves along an exterior surface of the at least foam portion of the earpiece.

In some embodiments of the system, the open first end of the hollow structure has a circular cross-section. In some embodiments, the open first end of the hollow structure has cross-section that includes a circular portion and a non-circular portion, wherein the non-circular portion of the cross-section is configured to prevent slippage or twisting of the at least foam portion of the earpiece while the at least foam portion is inserted into the sizer. In some embodiments, the open first end of the hollow structure has a triangular cross-section. In some embodiments, the open first end of the hollow structure has a rounded-corner triangular cross-section.

In some embodiments, the system further includes a container configured to store the earpiece, wherein the container includes a bottom portion that includes a hollow interior and an exterior, wherein the sizer is formed as part of the bottom portion, and a cap configured to removably couple to the bottom portion such that the container has a closed position where the hollow interior of the bottom portion is covered by the cap and an open position where the hollow interior of the bottom portion is uncovered.

In some embodiments of the system, the sizer is a stand-alone device, the system further including a container configured to store the earpiece and the sizer, wherein the container includes a bottom portion that includes a hollow interior and an exterior, and a cap configured to removably couple to the bottom portion such that the container has a closed position where the hollow interior of the bottom portion is covered by the cap and an open position where the hollow interior of the bottom portion is uncovered.

In some embodiments, the system further includes a container configured to store the earpiece, wherein the container includes a bottom portion that includes a hollow interior and an exterior, wherein the sizer is coupled to the exterior of the bottom portion via a tether (e.g., a string or other suitable connection device), and a cap configured to removably couple to the bottom portion such that the container has a closed position where the hollow interior of the bottom portion is covered by the cap and an open position where the hollow interior of the bottom portion is uncovered.

In some embodiments, the system further includes a container configured to store the earpiece, wherein the container includes a bottom portion that includes a hollow interior and an exterior, wherein the sizer is formed as part of the bottom portion, a cap configured to removably couple to the bottom portion such that the container has a closed position where the hollow interior of the bottom portion is covered by the cap and an open position where the hollow interior of the bottom portion is uncovered, and a connector coupled to the bottom portion and the cap such that the cap stays connected to the bottom portion when the container is in the open position.

In some embodiments, the system further includes a container configured to store the earpiece, wherein the container includes a bottom portion that includes a hollow interior and an exterior, wherein the sizer is formed as part of the bottom portion, and wherein the open first end of the sizer opens to the hollow interior of the bottom portion, and a cap configured to removably couple to the bottom portion such that the container has a closed position where the hollow interior of the bottom portion is covered by the cap and an open position where the hollow interior of the bottom portion is uncovered.

In some embodiments, the system further includes a container configured to store the earpiece, wherein the container includes a bottom portion that includes a hollow interior and an exterior, wherein the sizer is formed as part of the bottom portion, and wherein the open first end of the sizer opens to the exterior of the bottom portion, and a cap configured to removably couple to the bottom portion such that the container has a closed position where the hollow interior of the bottom portion is covered by the cap and an open position where the hollow interior of the bottom portion is uncovered.

In some embodiments, the system further include a container configured to store the earpiece, wherein the container includes a bottom portion that includes a hollow interior and an exterior, wherein the sizer is formed as part of the bottom portion, and wherein the open first end of the sizer opens to the exterior of the bottom portion, and a cap configured to removably couple to the bottom portion such that the container has a closed position where the hollow interior of the bottom portion is covered by the cap and an open position where the hollow interior of the bottom portion is uncovered, wherein the sizer further includes a center post that extends from the second end of the hollow structure toward the open first end of the hollow structure, wherein the center post is configured to keep the at least foam portion of the earpiece centered in the hollow structure, and a cleaning tool coupled to the second end of the hollow structure on a side of the second end opposite the open first end such that the cleaning tool is accessible from the hollow interior of the bottom portion of the container, and wherein the cleaning tool is configured to remove undesired material off of the earpiece.

In some embodiments, the system further includes a container configured to store the earpiece, wherein the container includes a bottom portion that includes a hollow interior and an exterior, wherein the sizer is formed as part of the bottom portion, and wherein the open first end of the sizer opens to the exterior of the bottom portion, and a cap configured to removably couple to the bottom portion such that the container has a closed position where the hollow interior of the bottom portion is covered by the cap and an open position where the hollow interior of the bottom portion is uncovered, wherein the sizer further includes a center post that extends from the second end of the hollow structure toward the open first end of the hollow structure, wherein the center post is configured to keep the at least foam portion of the earpiece centered in the hollow structure.

In some embodiments, the system further includes a container configured to store the earpiece, wherein the container includes a bottom portion that includes a hollow interior and an exterior, wherein the sizer is formed as part of the bottom portion, and wherein the open first end of the sizer opens to the hollow interior of the bottom portion, and a cap configured to removably couple to the bottom portion such that the container has a closed position where the hollow interior of the bottom portion is covered by the cap and an open position where the hollow interior of the bottom portion is uncovered, wherein the sizer further includes a center post that extends from the second end of the hollow structure toward the open first end of the hollow structure, wherein the center post is configured to keep the at least foam portion of the earpiece centered in the hollow structure.

In some embodiments, the system further includes a container configured to store the earpiece, wherein the container includes a bottom portion that includes a hollow interior and an exterior, wherein the sizer is formed as part of the bottom portion, and wherein the open first end of the sizer opens to the exterior of the bottom portion, and a cap configured to removably couple to the bottom portion such that the container has a closed position where the hollow interior of the bottom portion is covered by the cap and an open position where the hollow interior of the bottom portion is uncovered, wherein the sizer further includes a plurality of barbs or ridges located along an interior surface of the hollow structure, wherein the plurality of barbs/ridges is configured to hold the at least foam portion of the earpiece in place while the at least foam portion is inserted into the sizer.

In some embodiments, the present invention provides a method of shaping at least a foam portion of an earpiece, the method including providing a sizer having an open first end and a second end, wherein the first end has a first cross-sectional area, wherein the second end has a second cross-sectional area, and wherein the first cross-sectional area is larger than the second cross-sectional area; and reducing a size of at least the foam portion of the earpiece by inserting at least the foam portion of the earpiece into the sizer. In some embodiments, the sizer includes a conical portion closer to the first end and a cylindrical portion closer to the second end. In some embodiments, the second end is closed.

In some embodiments of the method, the sizer further includes a handle that extends from the second end of the hollow structure on a side of the second end opposite the open first end, the method further including holding the sizer by grasping the handle. In some embodiments of the method, the at least foam portion of the earpiece includes a center cavity, wherein the sizer further includes a center post that extends from the second end of the hollow structure toward the open first end of the hollow structure, the method further including centering the at least foam portion of the earpiece inside the sizer by aligning the center post such that the center post inserts into the center cavity of the at least foam portion of the earpiece. In some embodiments of the method, the sizer further includes a cleaning tool coupled to the second end of the hollow structure on a side of the second end opposite the open first end, the method further including removing undesired material off of the earpiece using the cleaning tool.

In some embodiments, the method further includes providing a container configured to store the earpiece, wherein the container includes a bottom portion that includes a hollow interior and an exterior, wherein the sizer is formed as part of the bottom portion, and a cap configured to removably couple to the bottom portion such that the container has a closed position where the hollow interior of the bottom portion is covered by the cap and an open position where the hollow interior of the bottom portion is uncovered. In some embodiments, the method further includes providing a container configured to store the earpiece and the sizer, wherein the container includes a bottom portion that includes a hollow interior and an exterior, and a cap configured to removably couple to the bottom portion such that the container has a closed position where the hollow interior of the bottom portion is covered by the cap and an open position where the hollow interior of the bottom portion is uncovered. In some embodiments, the method further includes providing a container configured to store the earpiece, wherein the container includes a bottom portion that includes a hollow interior and an exterior, wherein the sizer is formed as part of the bottom portion, a cap configured to removably couple to the bottom portion such that the container has a closed position where the hollow interior of the bottom portion is covered by the cap and an open position where the hollow interior of the bottom portion is uncovered; and connecting the cap to the bottom portion such that the cap stays connected to the bottom portion when the container is in the open position.

In some embodiments, the present invention provides a method of making a system for shaping at least a foam portion of an earpiece, the method including forming a sizer configured to receive at least the foam portion of the earpiece such that at least the foam portion of the earpiece is reduced in size before being placed into an ear of a user, wherein the forming of the sizer includes creating a hollow structure having an open first end and a second end, wherein the first end has a first cross-sectional area, wherein the second end has a second cross-sectional area, and wherein the first cross-sectional area is larger than the second cross-sectional area (in some embodiments, the sizer is made of a polymer material (e.g., plastic); in some embodiments, the sizer is made of any other suitable material (e.g., a metal); in some embodiments, the method is performed via plastic injection molding). In some embodiments, the hollow structure includes a conical portion closer to the first end and a cylindrical portion closer to the second end. In some embodiments, the second end is closed.

In some embodiments of the method, the forming of the sizer includes generating a handle that extends from the second end of the hollow structure on a side of the second end opposite the open first end, and wherein the handle is configured to provide a grip for the user to hold the sizer as a stand-alone device. In some embodiments of the method, the forming of the sizer includes generating a center post that extends from the second end of the hollow structure toward the open first end of the hollow structure, wherein the center post is configured to keep the at least foam portion of the earpiece centered in the hollow structure. In some embodiments of the method, the forming of the sizer includes generating a cleaning tool that extends from a side of the second end opposite the open first end, and wherein the cleaning tool is configured to remove undesired material off of the earpiece. In some embodiments of the method, the forming of the sizer includes generating a plurality of barbs or ridges located along an interior surface of the hollow structure, wherein the plurality of barbs/ridges is configured to hold the at least foam portion of the earpiece in place while the at least foam portion is inserted into the sizer.

In some embodiments of the method, the open first end of the hollow structure has a circular cross-section. In some embodiments, the open first end of the hollow structure has cross-section that includes a circular portion and a non-circular portion, wherein the non-circular portion of the cross-section is configured to prevent slippage of the at least foam portion of the earpiece while the at least foam portion is inserted into the sizer. In some embodiments, the open first end of the hollow structure has a triangular cross-section.

In some embodiments, the method further includes forming a container configured to store the earpiece, wherein the forming of the container includes creating a bottom portion that includes a hollow interior and an exterior, wherein the creating of the bottom portion includes the forming of the sizer such that the sizer is part of the bottom portion, and creating a cap configured to removably couple to the bottom portion such that the container has a closed position where the hollow interior of the bottom portion is covered by the cap and an open position where the hollow interior of the bottom portion is uncovered.

In some embodiments of the method, the sizer is a stand-alone device, the method further including forming a container configured to store the earpiece and the sizer, wherein the forming of the container includes creating a bottom portion that includes a hollow interior and an exterior, and creating a cap configured to removably couple to the bottom portion such that the container has a closed position where the hollow interior of the bottom portion is covered by the cap and an open position where the hollow interior of the bottom portion is uncovered.

In some embodiments, the method further includes forming a container configured to store the earpiece, wherein the forming of the container includes creating a bottom portion that includes a hollow interior and an exterior, coupling the sizer to the exterior of the bottom portion via a tether, and creating a cap configured to removably couple to the bottom portion such that the container has a closed position where the hollow interior of the bottom portion is covered by the cap and an open position where the hollow interior of the bottom portion is uncovered.

In some embodiments, the method further includes forming a container configured to store the earpiece, wherein the forming of the container includes creating a bottom portion that includes a hollow interior and an exterior, wherein the creating of the bottom portion includes the forming of the sizer such that the sizer is part of the bottom portion, creating a cap configured to removably couple to the bottom portion such that the container has a closed position where the hollow interior of the bottom portion is covered by the cap and an open position where the hollow interior of the bottom portion is uncovered; connecting the cap to the bottom portion such that the cap stays connected to the bottom portion when the container is in the open position.

In some embodiments, the method further includes forming a container configured to store the earpiece, wherein the forming of the container includes creating a bottom portion that includes a hollow interior and an exterior, wherein the creating of the bottom portion includes the forming of the sizer such that the sizer is part of the bottom portion, wherein the open first end of the sizer opens to the hollow interior of the bottom portion, and creating a cap configured to removably couple to the bottom portion such that the container has a closed position where the hollow interior of the bottom portion is covered by the cap and an open position where the hollow interior of the bottom portion is uncovered.

In some embodiments, the method further includes forming a container configured to store the earpiece, wherein the forming of the container includes creating a bottom portion that includes a hollow interior and an exterior, wherein the creating of the bottom portion includes the forming of the sizer such that the sizer is part of the bottom portion, wherein the open first end of the sizer opens to the exterior of the bottom portion, and creating a cap configured to removably couple to the bottom portion such that the container has a closed position where the hollow interior of the bottom portion is covered by the cap and an open position where the hollow interior of the bottom portion is uncovered.

In some embodiments, the method further includes forming a container configured to store the earpiece, wherein the forming of the container includes creating a bottom portion that includes a hollow interior and an exterior, wherein the creating of the bottom portion includes the forming of the sizer such that the sizer is part of the bottom portion, wherein the open first end of the sizer opens to the exterior of the bottom portion, and creating a cap configured to removably couple to the bottom portion such that the container has a closed position where the hollow interior of the bottom portion is covered by the cap and an open position where the hollow interior of the bottom portion is uncovered, wherein the forming of the sizer further includes generating a center post that extends from the second end of the hollow structure toward the open first end of the hollow structure, wherein the center post is configured to keep the at least foam portion of the earpiece centered in the hollow structure, and generating a cleaning tool that extends from a side of the second end opposite the open first end, and wherein the cleaning tool is configured to remove undesired material off of the earpiece.

In some embodiments, the method further includes forming a container configured to store the earpiece, wherein the forming of the container includes creating a bottom portion that includes a hollow interior and an exterior, wherein the creating of the bottom portion includes the forming of the sizer such that the sizer is part of the bottom portion, wherein the open first end of the sizer opens to the exterior of the bottom portion, and creating a cap configured to removably couple to the bottom portion such that the container has a closed position where the hollow interior of the bottom portion is covered by the cap and an open position where the hollow interior of the bottom portion is uncovered, wherein the forming of the sizer further includes generating a center post that extends from the second end of the hollow structure toward the open first end of the hollow structure, wherein the center post is configured to keep the at least foam portion of the earpiece centered in the hollow structure.

In some embodiments, the method further includes forming a container configured to store the earpiece, wherein the forming of the container includes creating a bottom portion that includes a hollow interior and an exterior, wherein the creating of the bottom portion includes the forming of the sizer such that the sizer is part of the bottom portion, wherein the open first end of the sizer opens to the hollow interior of the bottom portion, and creating a cap configured to removably couple to the bottom portion such that the container has a closed position where the hollow interior of the bottom portion is covered by the cap and an open position where the hollow interior of the bottom portion is uncovered, wherein the forming of the sizer further includes generating a center post that extends from the second end of the hollow structure toward the open first end of the hollow structure, wherein the center post is configured to keep the at least foam portion of the earpiece centered in the hollow structure.

In some embodiments, the method further includes forming a container configured to store the earpiece, wherein the forming of the container includes creating a bottom portion that includes a hollow interior and an exterior, wherein the creating of the bottom portion includes the forming of the sizer such that the sizer is part of the bottom portion, wherein the open first end of the sizer opens to the exterior of the bottom portion, and creating a cap configured to removably couple to the bottom portion such that the container has a closed position where the hollow interior of the bottom portion is covered by the cap and an open position where the hollow interior of the bottom portion is uncovered, wherein the forming of the sizer further includes generating a plurality of barbs or ridges located along an interior surface of the hollow structure, wherein the plurality of barbs/ridges is configured to hold the at least foam portion of the earpiece in place while the at least foam portion is inserted into the sizer.

In some embodiments, the present invention provides a system for shaping at least a foam portion of an earpiece configured to be placed in an ear of a user, the system including means for reducing a size of at least the foam portion of the earpiece. In some embodiments, the means for reducing includes means for holding the means for reducing. In some embodiments, the means for reducing includes means for centering the at least foam portion of the earpiece in the means for reducing. In some embodiments, the means for reducing includes means for removing undesired material off of the earpiece. In some embodiments, the means for reducing includes means for holding the at least foam portion of the earpiece in place while the at least foam portion is inserted into the means for reducing. In some embodiments, the earpiece is one of a plurality of earpieces, the system further including means for storing the plurality of earpieces, wherein the means for reducing is integral with the means for storing. In some embodiments, the system further includes means for storing the earpiece and the means for reducing. In some embodiments, the system further includes means for storing the earpiece; and means for coupling the means for reducing to an exterior of the means for storing. In some embodiments, the system further includes means for storing the earpiece, wherein the means for reducing is integral with the means for storing, wherein the means for reducing includes means for centering the at least foam portion of the earpiece in the means for reducing, and means for removing undesired material off of the earpiece.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A system for shaping at least a foam portion of an earpiece, the system comprising:
a sizer configured to receive at least the foam portion of the earpiece such that at least the foam portion of the earpiece is reduced in size before being placed into an ear of a user, wherein the sizer includes:
a hollow structure having an open first end and a second end, wherein the first end has a first cross-sectional area, wherein the second end has a second cross-sectional area, and wherein the first cross-sectional area is larger than the second cross-sectional area, and
a center post that extends from the second end of the hollow structure toward the open first end of the hollow structure, wherein the center post is configured to keep the at least foam portion of the earpiece centered in the hollow structure; and a container configured to store the earpiece, wherein the container includes:
a bottom portion that includes a hollow interior and an exterior, wherein the sizer is formed as part of the bottom portion, and wherein the open first end of the sizer opens to the exterior of the bottom portion, and
a cap configured to removably couple to the bottom portion such that the container has a closed position where the hollow interior of the bottom portion is covered by the cap and an open position where the hollow interior of the bottom portion is uncovered,
wherein the sizer further includes a plurality of ridges located along an interior surface of the hollow structure, wherein the plurality of ridges is configured to hold the at least foam portion of the earpiece in place while the at least foam portion is inserted into the sizer.

2. The system of claim 1, wherein the open first end of the hollow structure has cross-section that includes a circular portion and a non-circular portion, wherein the non-circular portion of the cross-section is configured to prevent slipping of the at least foam portion of the earpiece while the at least foam portion is inserted into the sizer.

3. The system of claim 1, wherein the sizer further includes a handle that extends from the second end of the hollow structure on a side of the second end opposite the open first end, and wherein the handle is configured to provide a grip for the user to hold the sizer as a stand-alone device.

4. The system of claim 1, wherein the container further includes a connector coupled to the bottom portion and the cap such that the cap stays connected to the bottom portion when the container is in the open position.

5. A system for shaping at least a foam portion of an earpiece, the system comprising:
a sizer configured to receive at least the foam portion of the earpiece such that at least the foam portion of the earpiece is reduced in size before being placed into an ear of a user, wherein the sizer includes:
a hollow structure having an open first end and a second end, wherein the first end has a first cross-sectional area, wherein the second end has a second cross-sectional area, and wherein the first cross-sectional area is larger than the second cross-sectional area, and
a plurality of ridges located along an interior surface of the hollow structure, wherein the plurality of ridges is configured to keep the at least foam portion of the earpiece from slipping while the at least foam portion is inserted into the sizer.

6. The system of claim 5, further comprising:
a container configured to store the earpiece, wherein the container includes:
a bottom portion that includes a hollow interior and an exterior, wherein the sizer is formed as part of the bottom portion,
a cap configured to removably couple to the bottom portion such that the container has a closed position where the hollow interior of the bottom portion is covered by the cap and an open position where the hollow interior of the bottom portion is uncovered, and
a connector coupled to the bottom portion and the cap such that the cap stays connected to the bottom portion when the container is in the open position.

7. The system of claim 5, wherein the sizer further includes a handle that extends from the second end of the hollow structure on a side of the second end opposite the open first end, and wherein the handle is configured to provide a grip for the user to hold the sizer as a stand-alone device.

8. The system of claim 5, wherein the open first end of the hollow structure has cross-section that includes a circular portion and a non-circular portion, wherein the non-circular portion of the cross-section is configured to prevent slipping of the at least foam portion of the earpiece while the at least foam portion is inserted into the sizer.

9. The system of claim 4, wherein the sizer further includes a center post that extends from the second end of the hollow structure toward the open first end of the hollow structure, wherein the center post is configured to keep the at least foam portion of the earpiece centered in the hollow structure.

10. The system of claim 5, further comprising:
a container configured to store the earpiece, wherein the container includes:
a bottom portion that includes a hollow interior and an exterior, wherein the sizer is coupled to the exterior of the bottom portion via a tether, and
a cap configured to removably couple to the bottom portion such that the container has a closed position where the hollow interior of the bottom portion is covered by the cap and an open position where the hollow interior of the bottom portion is uncovered.

11. The system of claim 5, further comprising:
a container configured to store the earpiece, wherein the container includes:
a bottom portion that includes a hollow interior and an exterior, wherein the sizer is formed as part of the bottom portion, and wherein the open first end of the sizer opens to the hollow interior of the bottom portion, and
a cap configured to removably couple to the bottom portion such that the container has a closed position where the hollow interior of the bottom portion is covered by the cap and an open position where the hollow interior of the bottom portion is uncovered.

12. The system of claim 5, further comprising:
a container configured to store the earpiece, wherein the container includes:
a bottom portion that includes a hollow interior and an exterior, wherein the sizer is formed as part of the bottom portion, and wherein the open first end of the sizer opens to the exterior of the bottom portion, and
a cap configured to removably couple to the bottom portion such that the container has a closed position where the hollow interior of the bottom portion is covered by the cap and an open position where the hollow interior of the bottom portion is uncovered.

13. The system of claim 5, further comprising:
a container configured to store the earpiece, wherein the container includes:
a bottom portion that includes a hollow interior and an exterior, wherein the sizer is formed as part of the bottom portion, and wherein the open first end of the sizer opens to the exterior of the bottom portion, and
a cap configured to removably couple to the bottom portion such that the container has a closed position where the hollow interior of the bottom portion is covered by the cap and an open position where the hollow interior of the bottom portion is uncovered,
wherein the sizer further includes:
a cleaning tool coupled to the second end of the hollow structure on a side of the second end opposite the open first end such that the cleaning tool is accessible from the hollow interior of the bottom portion of the container, and wherein the cleaning tool is configured to remove undesired material off of the earpiece.

14. A method of making a system for shaping at least a foam portion of an earpiece, the method comprising:
forming a sizer configured to receive at least the foam portion of the earpiece such that at least the foam portion of the earpiece is reduced in size before being placed into an ear of a user, wherein the forming of the sizer includes:
creating a hollow structure having an open first end and a second end, wherein the first end has a first cross-sectional area, wherein the second end has a second cross-sectional area, and wherein the first cross-sectional area is larger than the second cross-sectional area;
forming a plurality of ridges located along an interior surface of the hollow structure, wherein the plurality of ridges is configured to hold the at least foam portion of the earpiece in place while the at least foam portion is inserted into the sizer; and
forming a container configured to store the earpiece, wherein the forming of the container includes:
creating a bottom portion of the container, wherein the bottom portion includes a hollow interior and an exterior, wherein the creating of the bottom portion includes the forming of the sizer such that the sizer is part of the bottom portion, wherein the open first end of the sizer opens to the hollow interior of the bottom portion, and
creating a cap configured to removably couple to the bottom portion such that the container has a closed position where the hollow interior of the bottom portion is covered by the cap and an open position where the hollow interior of the bottom portion is uncovered.

15. The method of claim 14, wherein the forming of the sizer further includes:
generating a center post that extends from the second end of the hollow structure toward the open first end of the hollow structure, wherein the center post is configured to keep the at least foam portion of the earpiece centered in the hollow structure, and
generating a cleaning tool that extends from a side of the second end opposite the open first end, and wherein the cleaning tool is configured to remove undesired material off of the earpiece.

16. The method of claim 14, wherein the forming of the sizer further includes forming a handle that extends from the second end of the hollow structure on a side of the second end opposite the open first end, wherein the handle is configured to provide a grip for the user to hold the sizer as a stand-alone device.

17. The method of claim 14, wherein the open first end of the hollow structure has cross-section that includes a circular portion and a non-circular portion, wherein the non-circular portion of the cross-section is configured to prevent slipping of the at least foam portion of the earpiece while the at least foam portion is inserted into the sizer.

18. The method of claim 14, wherein the forming of the container further includes creating a connector coupled to the bottom portion and the cap such that the cap stays connected to the bottom portion when the container is in the open position.

19. The method of claim 14, wherein the forming of the sizer further includes:

forming a center post that extends from the second end of the hollow structure toward the open first end of the hollow structure, wherein the center post is configured to keep the at least foam portion of the earpiece centered in the hollow structure.

20. The method of claim 14, wherein the forming of the sizer further includes:

forming a cleaning tool that extends from a side of the second end opposite the open first end, wherein the cleaning tool is configured to remove undesired material off of the earpiece.

\* \* \* \* \*